United States Patent
Suehiro et al.

(10) Patent No.: US 10,180,395 B2
(45) Date of Patent: Jan. 15, 2019

(54) FUNCTIONAL WATER CONCENTRATION SENSOR

(71) Applicant: PANASONIC INTELLECTUAL PROPERTY MANAGEMENT CO., LTD., Osaka (JP)

(72) Inventors: Yoshifumi Suehiro, Osaka (JP); Toru Baba, Hyogo (JP); Shin Okumura, Osaka (JP); Takaaki Yoshihara, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/562,790

(22) PCT Filed: Jun. 15, 2016

(86) PCT No.: PCT/JP2016/002885
§ 371 (c)(1),
(2) Date: Sep. 28, 2017

(87) PCT Pub. No.: WO2017/010043
PCT Pub. Date: Jan. 19, 2017

(65) Prior Publication Data
US 2018/0284014 A1 Oct. 4, 2018

(30) Foreign Application Priority Data
Jul. 10, 2015 (JP) ................... 2015-139024

(51) Int. Cl.
*G01N 21/33* (2006.01)
*G01N 33/18* (2006.01)
*G01N 21/64* (2006.01)

(52) U.S. Cl.
CPC ........... *G01N 21/33* (2013.01); *G01N 21/645* (2013.01); *G01N 33/18* (2013.01); *G01N 2021/6482* (2013.01)

(58) Field of Classification Search
CPC ...... G01N 21/33; G01N 21/645; G01N 33/18; G01N 2021/6482
(Continued)

(56) References Cited

U.S. PATENT DOCUMENTS

| 3,247,413 A | 4/1966 | Bisso et al. |
| 3,591,801 A | 7/1971 | Watson |
| 6,940,600 B1 | 9/2005 | Smith |

FOREIGN PATENT DOCUMENTS

| GB | 1105975 A | 3/1968 |
| JP | S58-158541 A | 9/1983 |

(Continued)

OTHER PUBLICATIONS

Extended European Search Report issued in related European Application No. 16824029.9 dated Apr. 11, 2018.
(Continued)

*Primary Examiner* — Nicole Ippolito
*Assistant Examiner* — Hanway Chang
(74) *Attorney, Agent, or Firm* — McDermott Will & Emery LLP

(57) ABSTRACT

A functional water concentration sensor includes: a container used to contain functional water; a light source that emits ultraviolet light; a phosphor that emits fluorescence when excited by ultraviolet light emitted from the light source and transmitted through the container; and a light-receiving element that receives the fluorescence, wherein a peak wavelength of the ultraviolet light emitted from the light source is in a predetermined range that includes an absorption peak specific to the functional water.

17 Claims, 19 Drawing Sheets

(58) Field of Classification Search
USPC .............................................. 250/432 R, 428
See application file for complete search history.

(56) References Cited

FOREIGN PATENT DOCUMENTS

| | | |
|---|---|---|
| JP | H06-308026 | 11/1994 |
| JP | H10-267843 A | 10/1998 |
| JP | 2000-105195 A | 4/2000 |
| JP | 2002-005826 A | 1/2002 |
| JP | 2002-181694 A | 6/2002 |
| JP | 2002-543380 A | 12/2002 |
| JP | 2009-281911 A | 12/2009 |
| JP | 2014-092485 | 5/2014 |
| JP | 2016-136122 | 7/2016 |

OTHER PUBLICATIONS

International Search Report and Written Opinion issued in International Application No. PCT/JP2016/002885, dated on Aug. 16, 2016; with partial English translation.

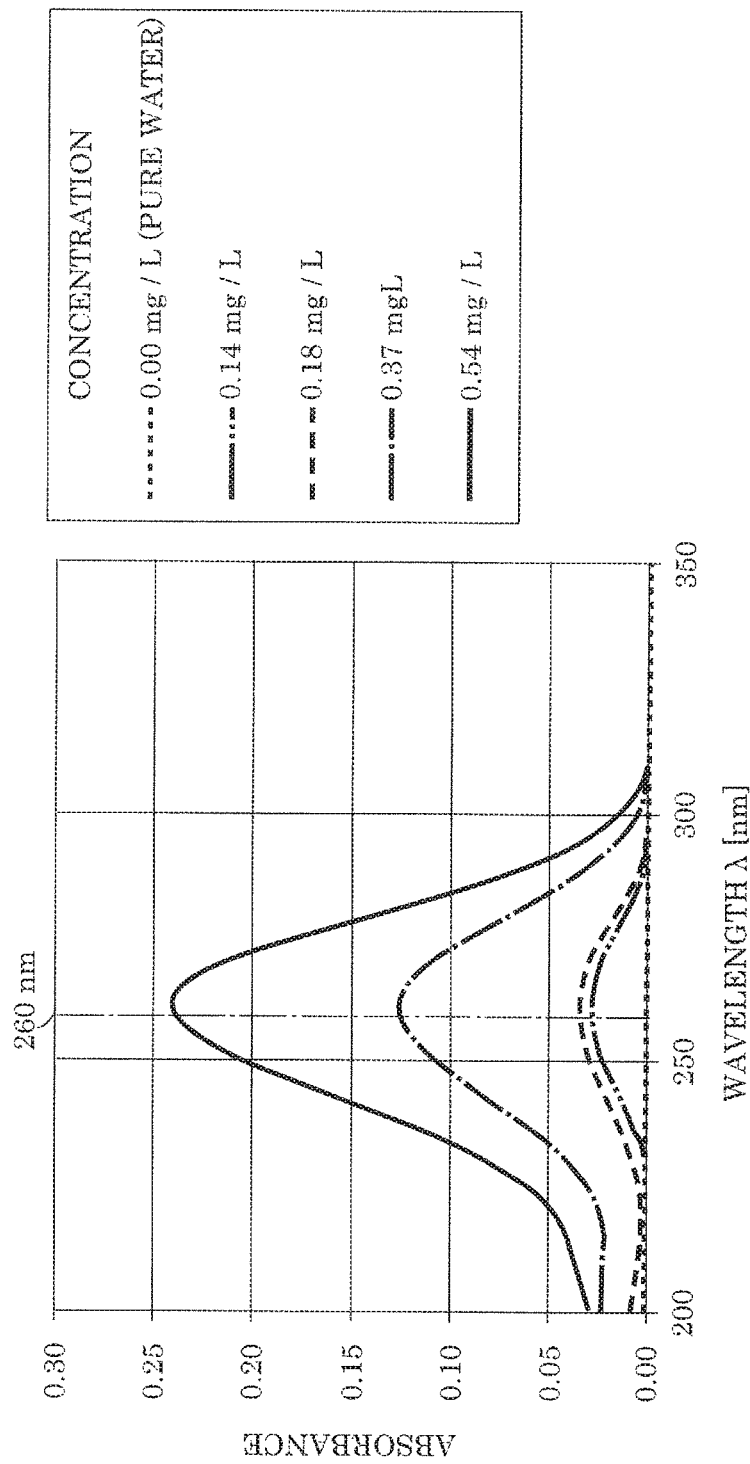

FUNCTIONAL WATER CONCENTRATION SENSOR

RELATED APPLICATIONS

This application is the U.S. National Phase under 35 U.S.C. § 371 of International Patent Application No. PCT/JP2016/002885, filed on Jun. 15, 2016, which in turn claims the benefit of Japanese Application No. 2015-139024, filed on Jul. 10, 2015, the entire disclosures of which Applications are incorporated by reference herein.

TECHNICAL FIELD

The present invention relates to a functional water concentration sensor.

BACKGROUND ART

Ozone has been conventionally used for sterilization, deodorization, bleaching, and so on. Ozone is a powerful oxidizing agent, and so its concentration needs to be controlled. Ozone concentration meters for measuring ozone concentration have thus been developed. For example, a light-absorption ozone concentration meter described in Patent Literature (PTL) 1 measures ozone concentration by irradiating a sample cell containing a sample with ultraviolet light and detecting the intensity of light transmitted through the sample cell.

CITATION LIST

Patent Literature

PTL 1: Japanese Unexamined Patent Application Publication No. 2002-5826

SUMMARY OF THE INVENTION

Technical Problem

There has been demand for compact and inexpensive sensors for detecting the concentration of functional water having predetermined functions, such as ozone. A compact sensor can be incorporated in, for example, a sterilization apparatus that uses functional water having sterilization capability. By detecting the concentration of the functional water in the sterilization apparatus, a decrease of the sterilization capability of the sterilization apparatus and the like can be determined appropriately. However, for example, the conventional ozone concentration meter mentioned above uses an expensive photodiode having sensitivity in the ultraviolet region. This makes it impossible to achieve a compact and inexpensive sensor.

The present invention accordingly has an object of providing a compact and inexpensive functional water concentration sensor.

Solution to Problem

A functional water concentration sensor according to an aspect of the present invention includes: a container used to contain functional water; a light source that emits ultraviolet light; a phosphor that emits fluorescence when excited by ultraviolet light emitted from the light source and transmitted through the container; and a light-receiving element that receives the fluorescence, wherein a peak wavelength of the ultraviolet light emitted from the light source is in a predetermined range that includes an absorption peak specific to the functional water.

Advantageous Effect of Invention

According to the present invention, a compact and inexpensive functional water concentration sensor can be provided.

BRIEF DESCRIPTION OF DRAWINGS

FIG. 6A is a diagram illustrating an absorption spectrum for each concentration of ozone water according to Embodiment 1 of the present invention.

DESCRIPTION OF EXEMPLARY EMBODIMENTS

Figure 1:
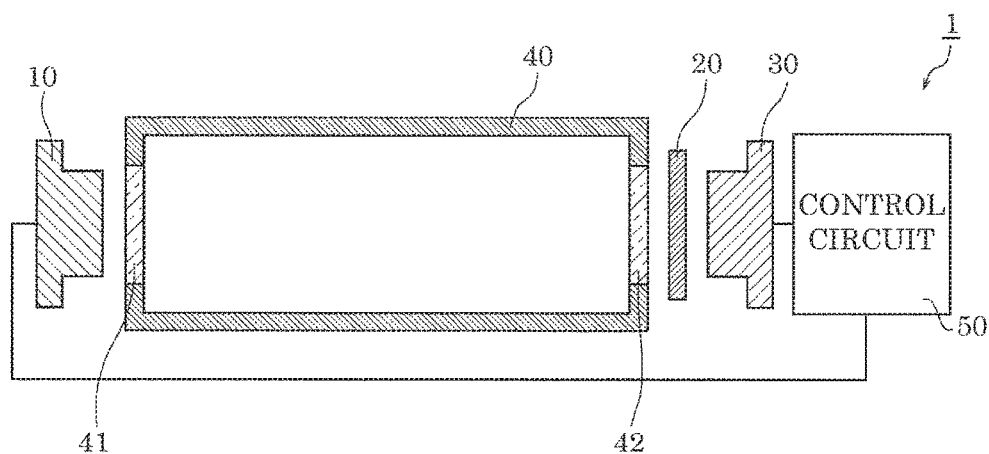
FIG. 1 is a schematic diagram illustrating the structure of a functional water concentration sensor according to Embodiment 1 of the present invention.

The following describes a functional water concentration sensor according to each embodiment of the present invention in detail, with reference to drawings. The embodiments described below each show a specific example of the present invention. The numerical values, shapes, materials, structural elements, the arrangement and connection of the structural elements, steps, the order of steps, etc. shown in the following embodiments are mere examples, and do not limit the scope of the present invention. Of the structural elements in the embodiments described below, the structural elements not recited in any one of the independent claims representing the broadest concepts of the present invention are described as optional structural elements.

Each drawing is a schematic and does not necessarily provide precise depiction. The same structural members are given the same reference marks in the drawings. Regarding the expressions such as "approximately all" and "approximately coincide" used in the embodiments, for example, "approximately coincide" means not only "exactly coincide" but also "substantially coincide", that is, coincidence with an error of about several %. The same applies to the other expressions including "approximately".

Embodiment 1

[Overview of Functional Water Concentration Sensor]

Figure 2:
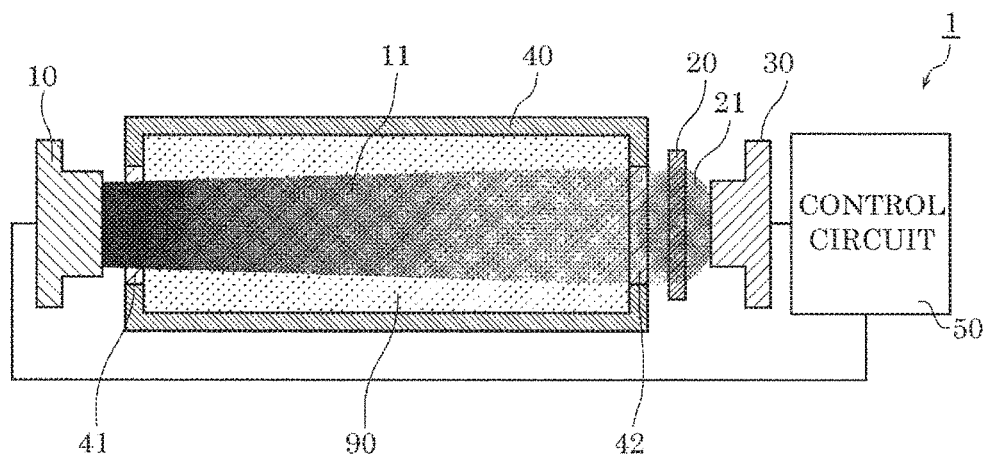
FIG. 2 is a schematic diagram illustrating the operation of the functional water concentration sensor according to Embodiment 1 of the present invention.

An overview of a functional water concentration sensor according to this embodiment is given first, with reference to FIGS. 1 and 2. FIG. 1 is a schematic diagram illustrating the structure of functional water concentration sensor 1 according to this embodiment. FIG. 2 is a schematic diagram illustrating the operation of functional water concentration sensor 1 according to this embodiment.

Functional water concentration sensor 1 according to this embodiment is a sensor for measuring the concentration of functional water 90 contained in container 40. In detail, functional water concentration sensor 1 irradiates functional water 90 with ultraviolet light, and wavelength-converts, by phosphor 20, ultraviolet light (transmitted light) after absorption while passing through functional water 90. Functional water concentration sensor 1 detects the wavelength-converted light (e.g. visible light), to measure the concentration of functional water 90.

Functional water 90 is an aqueous solution that is provided with a reproducible useful function by artificial treatment and whose function and process have been or are being found to be scientifically based. For example, functional water 90 is hypochlorous acid water, ozone water, or the like.

As illustrated in FIG. 1, functional water concentration sensor 1 according to this embodiment includes light source 10, phosphor 20, light-receiving element 30, container 40, and control circuit 50. Functional water concentration sensor 1 is placed in a light-blocking housing to prevent external light from entering light-receiving element 30, although not illustrated in FIG. 1. The inner surface of the housing may be made of a material that absorbs ultraviolet light, so as to absorb light (i.e. stray light) that has not entered entrance window 41 from among ultraviolet light 11 emitted from light source 10.

Each structural element in functional water concentration sensor 1 is described in detail below.

[Light Source]

Light source 10 emits ultraviolet light 11. Ultraviolet light 11 is, for example, light with a peak wavelength of 350 nm or less. Ultraviolet light 11 will be described in detail later.

Light source 10 may be capable of changing the peak wavelength of ultraviolet light 11. In detail, light source 10 may emit ultraviolet light 11 that differs in peak wavelength depending on functional water 90 to be measured. Thus, light source 10 may emit light with a peak wavelength set beforehand based on an absorption spectrum specific to functional water 90, as ultraviolet light 11.

Light source 10 is, for example, a solid-state light-emitting element such as a light emitting diode (LED) element, although not limited to such. Light source 10 may be a semiconductor laser, a compact mercury lamp, or the like.

As illustrated in FIG. 1, light source 10 is located in proximity to entrance window 41 of container 40. The term "in proximity to" means that the distance therebetween is within a predetermined range, and covers the case where they are in contact with each other. For example, the distance between light source 10 and entrance window 41 is 5 mm or less. Light source 10 is thus located so that approximately all ultraviolet light 11 emitted from light source 10 enters entrance window 41, i.e. emitted ultraviolet light 11 hardly leaks out of container 40. Ultraviolet light 11 from light source 10 enters entrance window 41 approximately perpendicularly, as illustrated in FIG. 2. The distance between light source 10 and entrance window 41 is not limited to the range of 5 mm or less.

[Phosphor]

Phosphor 20 emits fluorescence 21 when excited by ultraviolet light 11 emitted from light source 10 and transmitted through container 40. In detail, phosphor 20 wavelength-converts ultraviolet light 11 (transmitted light) transmitted through functional water 90, and emits the wavelength-converted light as fluorescence 21. For example, fluorescence 21 is visible light. In detail, phosphor 20 receives ultraviolet light 11, and emits fluorescence 21 whose peak wavelength is in the visible light region (380 nm to 780 nm).

Phosphor 20 may emit light having a peak wavelength corresponding to the sensitivity of light-receiving element 30, as fluorescence 21. In detail, phosphor 20 emits fluorescence 21 with a peak wavelength in a wavelength region where the sensitivity of light-receiving element 30 is high. For example, in the case where light-receiving element 30 has high sensitivity in the green region (500 nm to 570 nm), phosphor 20 may emit light whose peak wavelength is in the range of 500 nm to 570 nm, as fluorescence 21.

Figure 3:
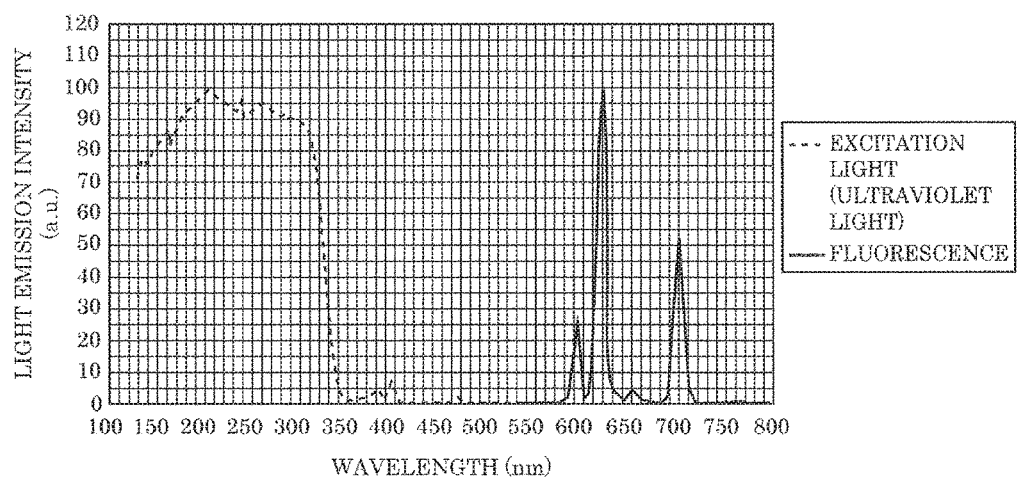
FIG. 3 is a diagram illustrating a fluorescence spectrum by an example of a phosphor according to Embodiment 1 of the present invention.
Figure 4:
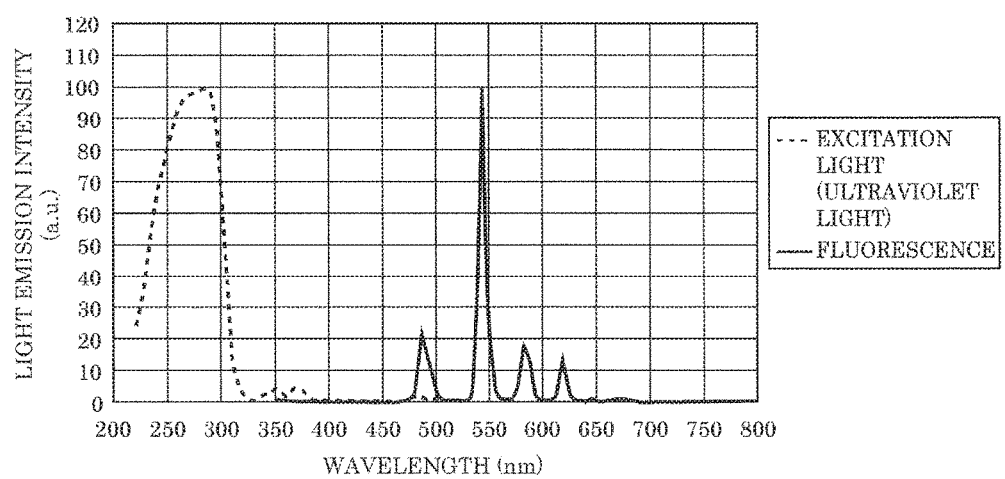
FIG. 4 is a diagram illustrating a fluorescence spectrum by another example of the phosphor according to Embodiment 1 of the present invention.

FIGS. 3 and 4 are each a diagram illustrating a fluorescence spectrum by an example of phosphor 20 according to this embodiment. In each of FIGS. 3 and 4, a dashed line indicates the spectrum of ultraviolet light 11 which is excitation light, and a solid line indicates the spectrum of fluorescence 21.

Phosphor 20 illustrated in FIG. 3 is a YPV phosphor (europium-activated yttrium phosphovanadate: $Y(P,V)O_4$: $Eu^{3+}$). As illustrated in FIG. 3, phosphor 20 emits fluorescence 21 (red light) with a peak wavelength of about 620 nm upon receiving ultraviolet light 11 of 350 nm or less.

Phosphor 20 illustrated in FIG. 4 is a LAP phosphor (cerium, terbium-activated lanthanum phosphate phosphor: $LaPO_4:Ce^{3+},Tb^{3+}$). As illustrated in FIG. 4, phosphor 20 emits fluorescence 21 (green light) with a peak wavelength of about 550 nm upon receiving ultraviolet light 11 of 300 nm or less.

In this embodiment, for example, phosphor 20 is provided at a light-transmitting plate such as a glass plate located in proximity to exit window 42. In detail, phosphor 20 is contained in a resin material applied to the surface of a glass plate. Alternatively, phosphor 20 may be dispersively contained in a glass plate. Alternatively, phosphor 20 may be dispersively contained in plate-like ceramic (e.g. alumina).

[Light-Receiving Element]

Light-receiving element 30 receives fluorescence 21. In detail, light-receiving element 30 photoelectrically converts received fluorescence 21, to generate an electric signal corresponding to the amount (i.e. intensity) of fluorescence 21 received. The generated electric signal is output to control circuit 50.

Light-receiving element 30 has high sensitivity in a predetermined wavelength region. In this embodiment, light-receiving element 30 has high sensitivity in the visible light region. In other words, light-receiving element 30 has higher sensitivity to visible light than to ultraviolet light. Light-receiving element 30 may have no sensitivity in the ultraviolet region (380 nm or less).

Light-receiving element 30 is, for example, a photodiode, although not limited to such. Light-receiving element 30 may be a phototransistor or the like. As light-receiving element 30, a general-purpose inexpensive photodiode having almost no sensitivity in the ultraviolet region may be used.

Light-receiving element 30 is located in proximity to phosphor 20. For example, the distance between light-receiving element 30 and phosphor 20 is 5 mm or less. Light-receiving element 30 may be in contact with phosphor 20. In detail, light-receiving element 30 is located so as to receive approximately all light traveling toward light-receiving element 30 from among fluorescence 21 emitted from phosphor 20. The distance between light-receiving element 30 and phosphor 20 is not limited to the range of 5 mm or less.

[Container]

Container 40 is a container for containing functional water 90. Container 40 is, for example, a bottomed cylindrical cell such as a bottomed circular cylinder or a bottomed rectangular cylinder, although not limited to such. Container 40 includes two transmission windows for transmitting ultraviolet light 11. In detail, container 40 includes entrance window 41 and exit window 42, as illustrated in FIG. 1.

Entrance window 41 is a window which ultraviolet light 11 emitted from light source 10 enters. Entrance window 41 is composed of a light-transmitting member that is located in an opening formed in container 40 and transmits ultraviolet light 11. For example, entrance window 41 (light-transmitting member) is made of silica glass, sapphire glass, or the like. In detail, entrance window 41 is plate-like glass whose entrance surface and exit surface are approximately flat. Ultraviolet light 11 enters entrance window 41 approximately perpendicularly. In detail, ultraviolet light 11 enters along the thickness direction of the plate-like glass (entrance window 41). Ultraviolet light 11 thus enters in the normal direction of the entrance surface.

Exit window 42 is a window from which ultraviolet light 11 that has entered container 40 exits toward phosphor 20. Exit window 42 is composed of a light-transmitting member that is located in an opening formed in container 40 and transmits ultraviolet light 11. For example, exit window 42 (light-transmitting member) is made of silica glass, sapphire glass, or the like. In detail, exit window 42 is plate-like glass whose entrance surface and exit surface are approximately flat. Ultraviolet light 11 exits from exit window 42 approximately perpendicularly. In detail, ultraviolet light 11 exits along the thickness direction of the plate-like glass (exit window 42). Ultraviolet light 11 thus exits in the normal direction of the exit surface.

In this embodiment, the body of container 40 (specifically, the part other than the two transmission windows) is made of a material that blocks (absorbs or reflects) ultraviolet light. For example, the body of container 40 is made of a resin material such as acrylic (PMMA) or polycarbonate (PC), or a metal material. Whole container 40 may have light-transmitting property for ultraviolet light 11. In detail, whole container 40 may be made of silica glass or the like.

In this embodiment, light source 10, container 40, phosphor 20, and light-receiving element 30 are arranged approximately in the same straight line in this order. As illustrated in FIG. 1, entrance window 41 and exit window 42 of container 40 are also arranged in this straight line. Hence, ultraviolet light 11 emitted from light source 10 reaches light-receiving element 30 in the shortest distance although wavelength-converted by phosphor 20 during the passage, as illustrated in FIG. 2. This suppresses the occurrence of light leakage (stray light) between light source 10 and light-receiving element 30, so that the intensity of fluorescence 21 can be accurately detected to measure the concentration of functional water 90 accurately.

Container 40 may be a part of predetermined piping. In detail, functional water 90 may flow inside container 40. For example, functional water 90 may circulate between container 40 and a reaction tank (not illustrated). The reaction tank is a container for causing functional water 90 to achieve its function. For example, in the case where functional water 90 has a function such as sterilization or deodorization, functional water 90 comes into contact with a subject (e.g.

gas such as air) in the reaction tank to sterilize or deodorize the subject. In this case, while functional water 90 is performing sterilization or deodorization, functional water concentration sensor 1 can measure the concentration of functional water 90. Functional water concentration sensor 1 can thus be incorporated in a deodorization apparatus or the like.

[Control Circuit]

Control circuit 50 is a controller that controls light source 10 and light-receiving element 30. Control circuit 50 includes nonvolatile memory storing a program, volatile memory which is a temporary storage area for executing the program, an input/output port, and a processor for executing the program. Control circuit 50 is, for example, a microcomputer (microcontroller) or the like.

Control circuit 50 measures (calculates) the concentration of functional water 90 based on the electric signal output from light-receiving element 30. In detail, control circuit 50 calculates the intensity of fluorescence 21 based on the electric signal, and calculates the transmittance (or absorbance) of functional water 90 based on the calculated intensity of fluorescence 21. Control circuit 50 calculates the concentration of functional water 90 from the calculated transmittance, based on the Lambert-Beer law described later. Control circuit 50 may store a table associating the intensity of fluorescence 21 and the concentration of functional water 90 with each other in memory beforehand, and determine the concentration of functional water 90 with reference to the table.

Control circuit 50 may also control the turning on and off of light source 10, the intensity and wavelength of ultraviolet light 11, and the like. In detail, control circuit 50 causes light source 10 to emit ultraviolet light 11 with a predetermined intensity and wavelength at predetermined timing, based on the user's instruction, the program, or the like. For example, control circuit 50 may change the intensity and wavelength of ultraviolet light 11 based on the type of functional water 90.

Control circuit 50 may perform feedback control on light source 10, based on the result of measuring the concentration of functional water 90. For example, in the case where the amount of light detected by light-receiving element 30 is excessively small, i.e. in the case where the concentration of functional water 90 is excessively high, control circuit 50 may increase the intensity of ultraviolet light 11 or change the wavelength of ultraviolet light 11.

[Ultraviolet Light]

Ultraviolet light 11 emitted from light source 10 according to this embodiment is described in detail below.

The peak wavelength of ultraviolet light 11 emitted from light source 10 (ultraviolet light before being transmitted through functional water 90) is in a predetermined range that includes an absorption peak specific to functional water 90. The absorption peak is a wavelength showing maximum absorbance in the absorption spectrum of functional water 90. In other words, the absorption peak is the wavelength of light at which the absorption by functional water 90 is the maximum.

The following describes the relationship between the concentration of functional water 90 and the absorbance of ultraviolet light 11 by functional water 90. When the intensity of light (incoming light) before entering a medium is denoted by $I_0$ and the intensity of light (transmitted light) after being transmitted through the medium having a length L is denoted by I, the following (Expression 1) and (Expression 2) are typically satisfied according to the Lambert-Beer law.

[Math. 1]

$$\text{transmittance} = (\text{intensity } I \text{ of transmitted light})/(\text{intensity } I_0 \text{ of incoming light}) = e^{-aLC} \quad \text{(Expression 1)}$$

$$\text{absorbance} = 1 - \text{transmittance}. \quad \text{(Expression 2)}$$

Here, "a" is an absorption coefficient, and "C" is the molar concentration of the medium. "L" is the length (i.e. optical path length) of the medium (i.e. functional water 90) through which ultraviolet light 11 is transmitted, and corresponds to the distance from entrance window 41 to exit window 42 of container 40 in this embodiment.

The absorbance represents the absorption ratio of ultraviolet light 11 by functional water 90. Higher absorbance means more absorption by functional water 90. For example, absorbance "1" indicates that all ultraviolet light 11 are absorbed, and absorbance "0" indicates that no ultraviolet light 11 is absorbed. The transmittance represents the transmission ratio of ultraviolet light 11 by functional water 90.

Figure 5A:
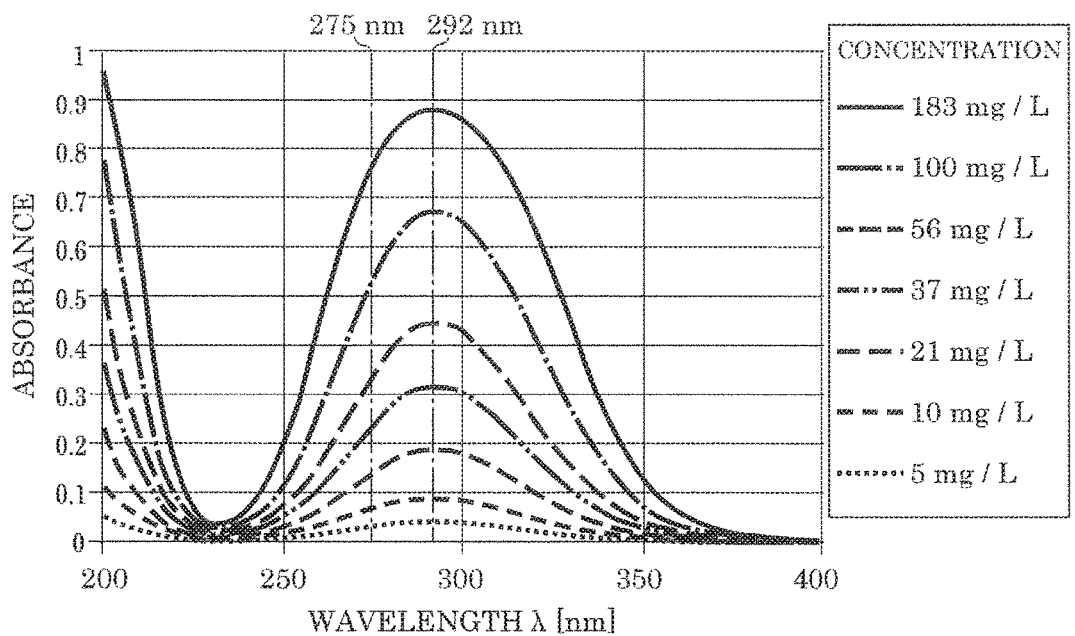
FIG. 5A is a diagram illustrating an absorption spectrum for each concentration of hypochlorous acid water according to Embodiment 1 of the present invention.

FIG. 5A is a diagram illustrating an absorption spectrum for each concentration of hypochlorous acid water according to this embodiment. In FIG. 5A, the horizontal axis represents the wavelength of light (ultraviolet light 11) with which functional water 90 (hypochlorous acid water) is irradiated, and the vertical axis represents the absorbance of functional water 90.

As illustrated in FIG. 5A, hypochlorous acid water has an absorption peak of about 292 nm regardless of its concentration, and absorbs a lot of light in a predetermined range including the absorption peak. The predetermined range is a range of absorbance of at least a predetermined proportion of the absorbance at the absorption peak. The predetermined proportion is, for example, 5% to 20%. For example, the predetermined range of ultraviolet light absorbable by hypochlorous acid water is 250 nm or more and 350 nm or less. Hence, in this embodiment, in the case where functional water 90 is hypochlorous acid water, light source 10 emits ultraviolet light 11 whose peak wavelength is in the range of 250 nm to 350 nm.

In the predetermined range including the absorption peak, the absorbance for light of a predetermined wavelength is higher when the concentration of hypochlorous acid water is higher, and lower when the concentration of hypochlorous acid water is lower. This tendency is noticeable around the absorption peak of about 292 nm, as illustrated in FIG. 5A.

Figure 5B:
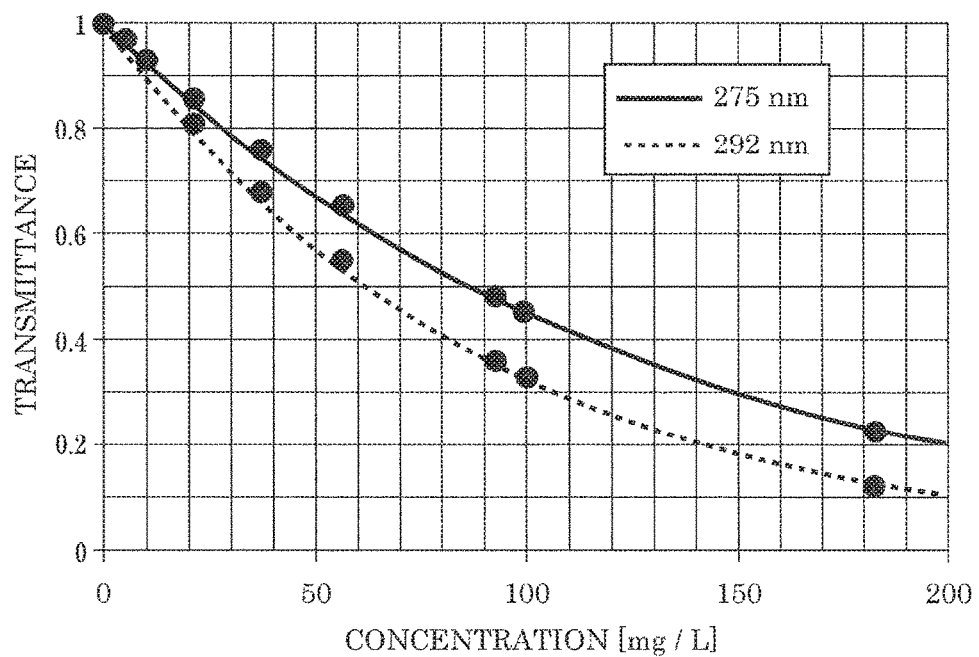
FIG. 5B is a diagram illustrating the transmittance of ultraviolet light with respect to the concentration of hypochlorous acid water according to Embodiment 1 of the present invention.

FIG. 5B is a diagram illustrating the transmittance of ultraviolet light with respect to the concentration of hypochlorous acid water according to this embodiment. In FIG. 5B, the horizontal axis represents the concentration of functional water 90, and the vertical axis represents the transmittance of functional water 90 for ultraviolet light 11.

In FIG. 5B, black circles represent measured values, and a solid line and a dashed line each represent an exponential approximation curve of the measured values obtained by the least-squares method based on (Expression 1).

The rate of change in transmittance with respect to the change in concentration is higher for light with a wavelength of 292 nm than for light with a wavelength of 275 nm. In other words, when ultraviolet light 11 is closer to the absorption peak in the absorption spectrum, the concentration of functional water 90 can be calculated based on the transmittance more easily.

FIG. 6A is a diagram illustrating an absorption spectrum for each concentration of ozone water according to this embodiment. In FIG. 6A, the horizontal axis represents the wavelength of light (ultraviolet light 11) with which functional water 90 (ozone water) is irradiated, and the vertical axis represents the absorbance of functional water 90.

As illustrated in FIG. 6A, ozone water has an absorption peak of about 260 nm regardless of its concentration, and absorbs a lot of light in a predetermined range including the absorption peak. For example, the predetermined range of ultraviolet light absorbable by ozone water is 220 nm or more and 300 nm or less. Hence, in this embodiment, in the case where functional water 90 is ozone water, light source 10 emits ultraviolet light 11 whose peak wavelength is in the range of 220 nm to 300 nm.

In the predetermined range including the absorption peak, the absorbance for a predetermined wavelength is higher when the concentration of ozone water is higher, and lower when the concentration of ozone water is lower, as in the case of hypochlorous acid water. This tendency is noticeable around the absorption peak of about 260 nm, as illustrated in FIG. 6A.

Figure 6B:
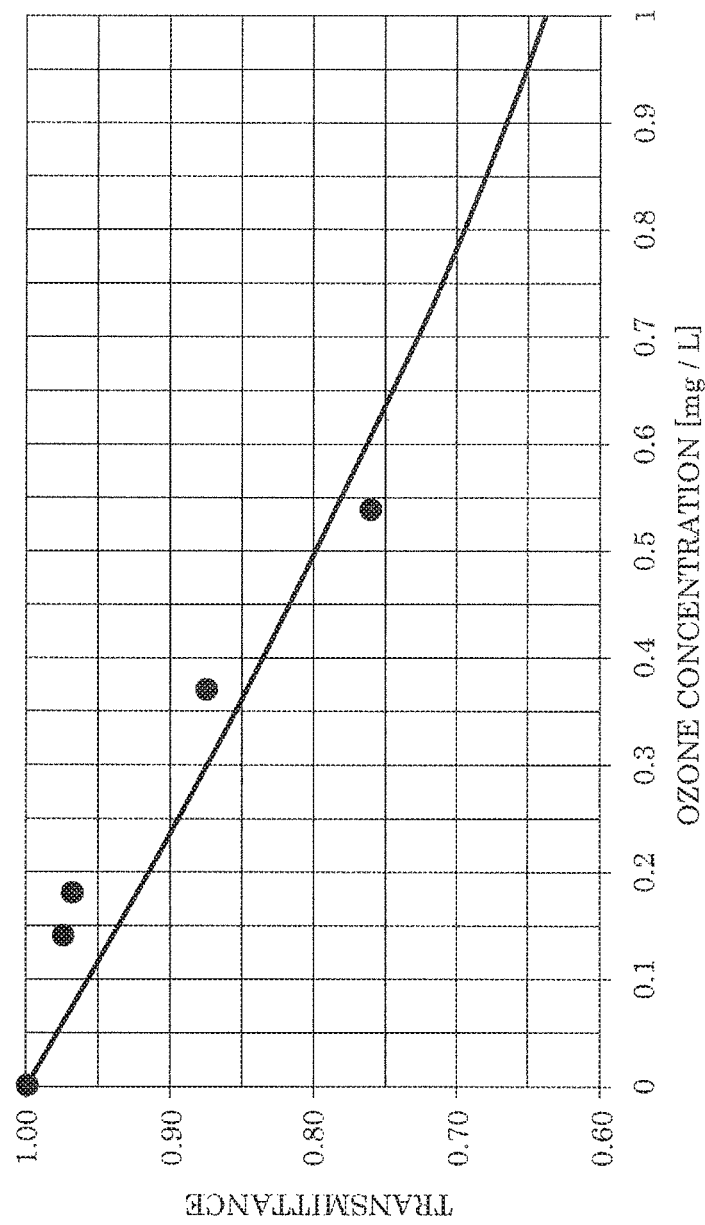
FIG. 6B is a diagram illustrating the transmittance of ultraviolet light with respect to the concentration of ozone water according to Embodiment 1 of the present invention.

FIG. 6B is a diagram illustrating the transmittance of ultraviolet light with respect to the concentration of ozone water according to this embodiment. In FIG. 6B, the horizontal axis represents the concentration of functional water 90, and the vertical axis represents the transmittance of functional water 90 for ultraviolet light 11. Black circles represent measured values, and a solid line represents an exponential approximation curve of the measured values obtained by the least-squares method.

FIG. 6B illustrates the transmittance with respect to the ozone concentration in the case of applying light of 260 nm in wavelength. The transmittance is lower when the ozone concentration is higher, as illustrated in FIG. 6B.

As illustrated in FIGS. 5B and 6B, the transmittance and the concentration of functional water 90 have a dependency relationship based on the Lambert-Beer law. Therefore, by obtaining the intensity of incoming light before being transmitted through functional water 90 and the intensity of transmitted light (outgoing light) after being transmitted through functional water 90, the absorbance (or transmittance) of functional water 90 can be calculated based on (Expression 1).

Thus, in this embodiment, in the case where functional water 90 is hypochlorous acid water, light source 10 emits light whose peak wavelength is in the range of 250 nm to 350 nm, as ultraviolet light 11. For example, light source 10 emits light whose peak wavelength is 275 nm, as ultraviolet light 11.

In the case where functional water 90 is ozone water, light source 10 emits light whose peak wavelength is in the range of 220 nm to 300 nm, as ultraviolet light 11. For example, light source 10 emits light whose peak wavelength is 260 nm, as ultraviolet light 11.

[Measurement of Concentration of Functional Water]

As described above, in this embodiment, the concentration of functional water 90 is measured based on the intensity of ultraviolet light 11 before entrance and the intensity of ultraviolet light 11 after transmission. In detail, ultraviolet light 11 which is transmitted light is not directly detected, but the light is converted into fluorescence 21 by phosphor 20 and fluorescence 21 after the conversion is detected by light-receiving element 30. In this embodiment, the intensity of fluorescence 21 is used instead of the intensity of the transmitted light (ultraviolet light 11), to measure the concentration of functional water 90.

First, to examine that the concentration of functional water 90 can be correctly measured based on the intensity of ultraviolet light 11, the result of directly detecting the intensity of ultraviolet light 11 after transmission without using phosphor 20 is described below, with reference to FIG. 7.

Figure 7:
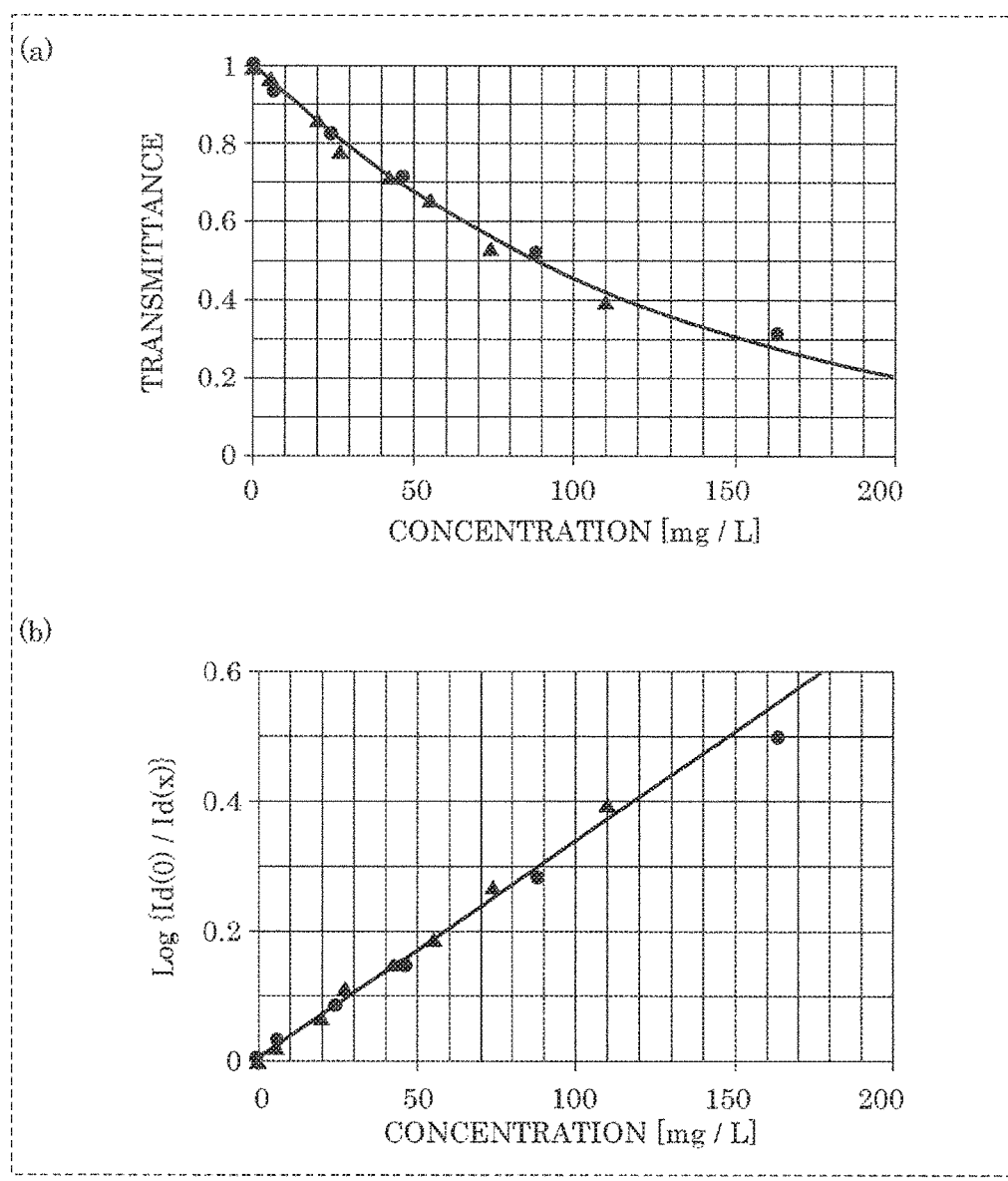
FIG. 7 is a diagram illustrating the relationship between the concentration of hypochlorous acid water and the transmittance of ultraviolet light in the case of not providing the phosphor according to Embodiment 1 of the present invention.

FIG. 7 is a diagram illustrating the relationship between the concentration of hypochlorous acid water and the transmittance of ultraviolet light 11 in the case of not providing phosphor 20 according to this embodiment. In FIG. 7, black circles and black triangles represent measured values, and a solid line represents an exponential approximation curve of the measured values obtained by the least-squares method.

In FIG. 7, transmitted light (ultraviolet light 11) emitted from exit window 42 is detected using a photodiode having sensitivity in the ultraviolet region, without phosphor 20. (a) in FIG. 7 illustrates the case where the peak wavelength of ultraviolet light 11 is 275 nm, which is the same as the graph in FIG. 5B. (b) in FIG. 7 illustrates the result of logarithmically converting the vertical axis of the graph illustrated in (a).

Based on the Lambert-Beer law, the transmittance is expressed as an exponential function of the concentration as shown in (Expression 1). The relationship between the transmittance and the concentration is accordingly expressed by a straight line in a logarithmic graph. As illustrated in (b) in FIG. 7, the measured values (black circles and black triangles) approximately coincide with the approximation straight line. This demonstrates that the concentration of functional water 90 can be measured by detecting ultraviolet light 11.

The result of using phosphor 20 is described next, with reference to FIG. 8.

Figure 8:
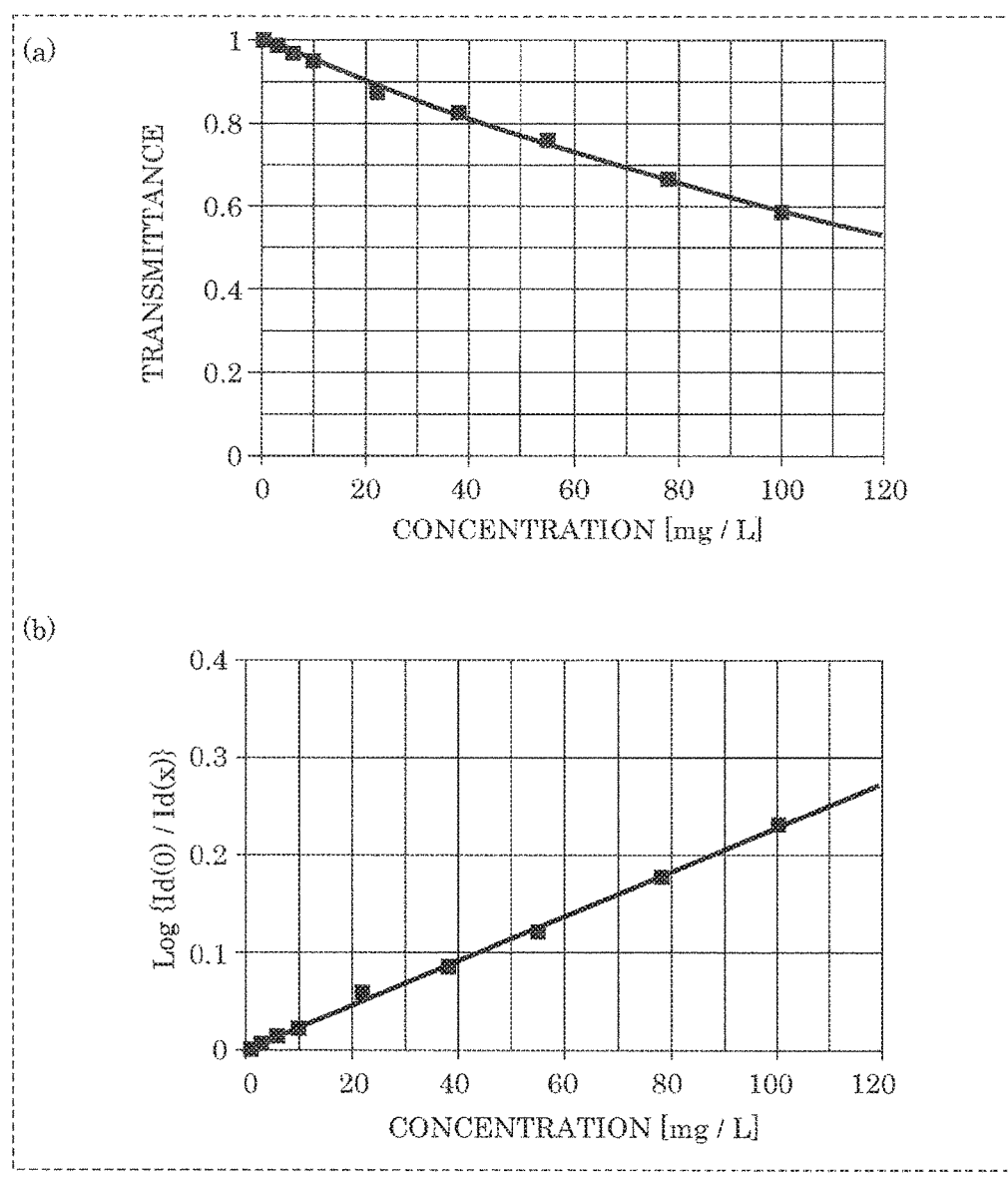
FIG. 8 is a diagram illustrating the relationship between the concentration of hypochlorous acid water and the transmittance of ultraviolet light according to Embodiment 1 of the present invention.

FIG. 8 is a diagram illustrating the relationship between the concentration of hypochlorous acid water and the transmittance of ultraviolet light according to this embodiment. In FIG. 8, black squares represent measured values, and a solid line represents an exponential approximation curve of the measured values obtained by the least-squares method.

In FIG. 8, a YPV phosphor is used as phosphor 20. Phosphor 20 emits fluorescence 21 whose intensity corresponds to the intensity of ultraviolet light 11 which is excitation light. In detail, ultraviolet light 11 as excitation light and fluorescence 21 are in a proportional relationship. Accordingly, control circuit 50 calculates the transmittance of ultraviolet light 11, by converting the intensity of fluorescence 21 detected by light-receiving element 30 into the intensity of ultraviolet light 11.

(a) in FIG. 8 illustrates the case where the peak wavelength of ultraviolet light 11 is 275 nm. (b) in FIG. 8 illustrates the result of converting the graph illustrated in (a) into a logarithmic graph. As illustrated in (b) in FIG. 8, in the case of detecting fluorescence 21, too, the measured values (black squares) approximately coincide with the approximation curve (solid line), as in the case of directly detecting ultraviolet light 11. This demonstrates that the concentration of functional water 90 can be measured by detecting fluorescence 21. In other words, there is no need to directly detect ultraviolet light 11.

[Advantageous Effects, Etc.]

As described above, functional water concentration sensor 1 according to this embodiment includes: container 40 used to contain functional water 90; light source 10 that emits ultraviolet light 11; phosphor 20 that emits fluorescence 21 when excited by ultraviolet light 11 emitted from light source 10 and transmitted through container 40; and light-receiving element 30 that receives fluorescence 21, wherein a peak wavelength of ultraviolet light 11 emitted from light source 10 is in a predetermined range that includes an absorption peak specific to functional water 90.

Thus, phosphor 20 wavelength-converts ultraviolet light 11 to emit fluorescence 21, and light-receiving element 30 receives fluorescence 21 emitted from phosphor 20. Fluorescence 21 is light longer in wavelength than ultraviolet light 11, such as visible light. Since light-receiving element 30 does not need to have sensitivity in the ultraviolet region, an inexpensive photodiode having sensitivity in the visible light region can be used as light-receiving element 30.

For example, an LED element which is compact and long-life can be used as light source 10. Functional water concentration sensor 1 can thus be reduced in size and increased in life.

In this embodiment, ultraviolet light 11 emitted from light source 10 is determined so that its peak wavelength is in the predetermined range including the absorption peak specific to functional water 90, based on, for example, an absorption spectrum specific to functional water 90. In detail, by absorbing ultraviolet light 11 by functional water 90 to detect a change in intensity of ultraviolet light 11, the concentration of functional water 90 is measured. Accordingly, a substance for measuring the concentration, such as a detection agent, need not be added to functional water 90. Since functional water 90 is prevented from reacting with such a detection agent and changing chemically, functional water 90 can function properly even after its concentration is measured (i.e. after being irradiated with ultraviolet light 11). Thus, functional water concentration sensor 1 can measure the concentration while maintaining the function of functional water 90, and so can be incorporated in, for example, an apparatus that utilizes functional water 90.

For example, in the case where functional water 90 is a liquid having sterilization capability such as hypochlorous acid water, the sterilization capability of functional water 90 is not lost, so that functional water 90 can be used for sterilization. As an example, concentration measurement and sterilization can be performed while circulating functional water 90. This enables feedback control such as reflecting the concentration measurement result in the sterilization. Functional water concentration sensor 1 can thus be incorporated in equipment such as a sterilization apparatus.

For example, in the case where functional water 90 is used for sterilization or the like and as a result the concentration of functional water 90 decreases, feedback control such as adding functional water 90 is performed. This increases the concentration of functional water 90, as a result of which functional water 90 achieves its function such as sterilization sufficiently. Feedback control may also be performed to prevent the concentration of functional water 90 from becoming excessively high, thus preventing the generation of harmful gas or odorous gas.

For example, phosphor 20 emits light having a peak wavelength corresponding to sensitivity of light-receiving element 30, as fluorescence 21.

Thus, for example, the region where the sensitivity of light-receiving element 30 is high can be used effectively. This widens the detectable light amount range. Consequently, the measurable concentration range can be widened, or concentration measurement accuracy can be enhanced.

In this embodiment, phosphor 20 uniformly produces fluorescence omnidirectionally. In other words, fluorescence 21 emitted from phosphor 20 is omnidirectional. Accordingly, in the case where phosphor 20 and light-receiving element 30 are away from each other, the amount of fluorescence 21 received by light-receiving element 30 decreases.

In view of this, in functional water concentration sensor 1 according to this embodiment, for example, light-receiving element 30 is located in proximity to phosphor 20.

The amount of light entering light-receiving element 30 from among fluorescence 21 emitted from phosphor 20 can thus be increased, with it being possible to detect even weak fluorescence 21. Consequently, the measurable concentration range can be widened. In addition, light (stray light) traveling in the housing (not illustrated) of functional water concentration sensor 1 without entering light-receiving element 30 can be reduced. This reduces detection errors caused by stray light entering light-receiving element 30, and enables accurate detection of fluorescence 21.

For example, light source 10, container 40, phosphor 20, and light-receiving element 30 are arranged approximately in a same straight line in the stated order.

This makes it unnecessary to change the traveling direction of ultraviolet light 11 or fluorescence 21 by reflection, refraction, or the like. Since a member such as a lens or a mirror need not be provided, reductions in size and cost can be achieved. If a member such as a lens or a mirror is used to change the traveling direction of light, there is a possibility that the amount of fluorescence 21 entering light-receiving element 30 decreases due to the occurrence of stray light, light absorption by the member, or the like. Functional water concentration sensor 1 does not include such a lens or mirror, and so can prevent a decrease in the amount of fluorescence 21 entering light-receiving element 30 and accurately measure the concentration of functional water 90.

For example, container 40 includes entrance window 41 which ultraviolet light 11 emitted from light source 10 enters, and ultraviolet light 11 emitted from light source 10 enters entrance window 41 approximately perpendicularly.

Ultraviolet light 11 can thus be prevented from refraction and reflection at the entrance surface of entrance window 41. Since the light emitted from light source 10 is efficiently applied to functional water 90 in container 40, the concentration of functional water 90 can be measured accurately.

The following describes variations of functional water concentration sensor 1 according to this embodiment, with reference to drawings. In each variation, the description of the same parts as those of functional water concentration sensor 1 according to this embodiment is omitted or abridged.

[Variation 1]

Figure 9:
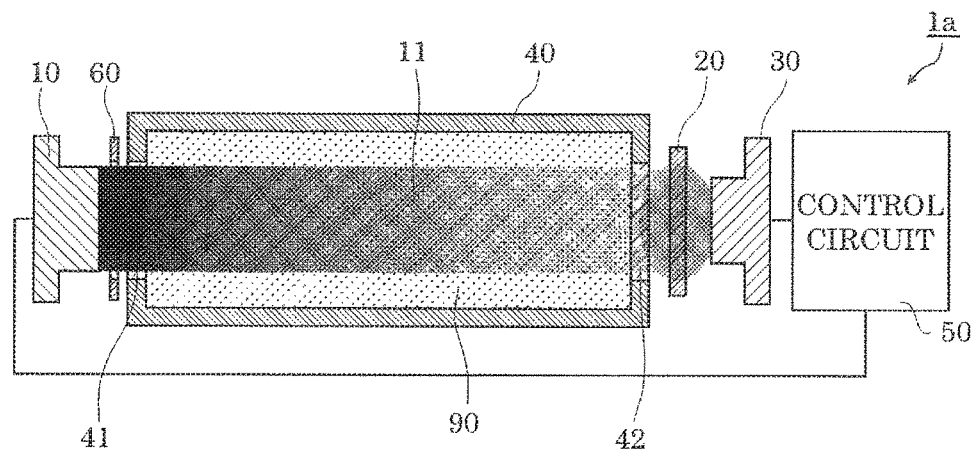
FIG. 9 is a schematic diagram illustrating the structure and operation of a functional water concentration sensor according to Variation 1 of Embodiment 1 of the present invention.

FIG. 9 is a schematic diagram illustrating the structure and operation of functional water concentration sensor 1a according to Variation 1 of this embodiment.

Functional water concentration sensor 1a according to this variation differs from functional water concentration sensor 1 illustrated in FIG. 1 in that slit portion 60 is added.

Slit portion 60 is located between light source 10 and entrance window 41, and limits the application range of ultraviolet light 11. In detail, slit portion 60 has an opening having approximately the same shape as entrance window 41. Slit portion 60 is, for example, a plate having an opening (slit). Slit portion 60 is located so that its opening approximately coincides with entrance window 41 when viewed from light source 10.

Slit portion 60 is made of a material that blocks (reflects or absorbs) ultraviolet light 11. For example, slit portion 60 is made of the same material as the body of container 40.

As described above, in functional water concentration sensor 1a according to this variation, light applied to parts other than the opening from among ultraviolet light 11 emitted from light source 10 is blocked by slit portion 60 so as not to travel into container 40. Light that has passed through the opening enters entrance window 41, is transmitted through functional water 90, and exits from exit window 42. Stray light caused by applying ultraviolet light to unnecessary regions can thus be reduced to enhance detection accuracy.

[Variation 2]

Figure 10:
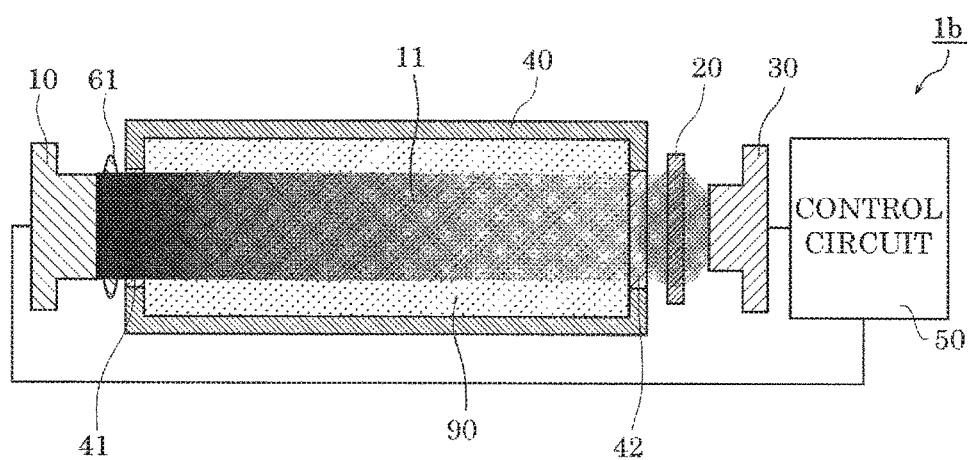
FIG. 10 is a schematic diagram illustrating the structure and operation of a functional water concentration sensor according to Variation 2 of Embodiment 1 of the present invention.

FIG. 10 is a schematic diagram illustrating the structure and operation of functional water concentration sensor 1b according to Variation 2 of this embodiment.

Functional water concentration sensor 1b according to this variation differs from functional water concentration sensor 1 illustrated in FIG. 1 in that lens portion 61 is added.

Lens portion 61 is located between light source 10 and entrance window 41, and suppresses divergence of ultraviolet light 11. Lens portion 61 is, for example, a condenser lens for condensing light to phosphor 20, or a collimator lens for emitting ultraviolet light 11 as parallel light. For example, lens portion 61 is made of silica glass having light-transmitting property.

As described above, in functional water concentration sensor 1b according to this variation, the amount of ultraviolet light 11 transmitted through functional water 90 can be increased. Consequently, the measurable concentration range can be widened, or concentration measurement accuracy can be enhanced.

[Variation 3]

Figure 11:
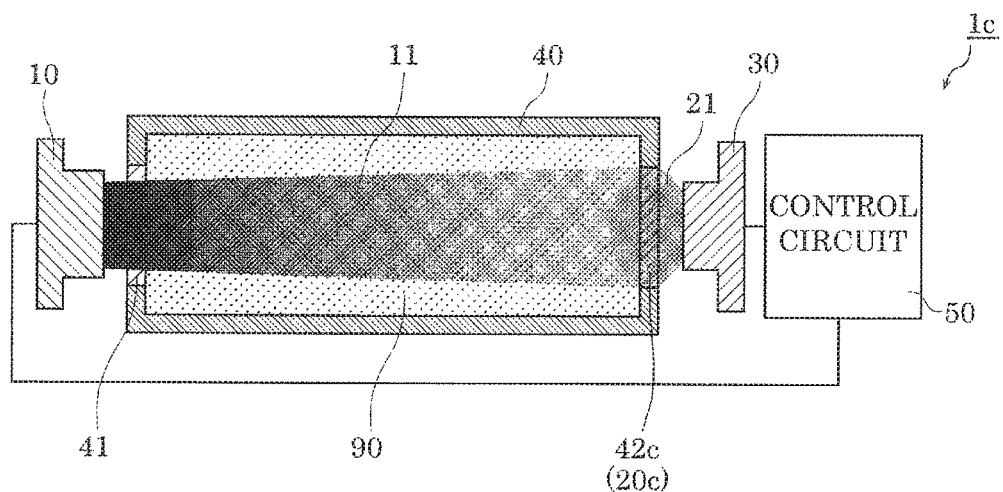
FIG. 11 is a schematic diagram illustrating the structure and operation of a functional water concentration sensor according to Variation 3 of Embodiment 1 of the present invention.

FIG. 11 is a schematic diagram illustrating the structure and operation of functional water concentration sensor 1c according to Variation 3 of this embodiment.

Functional water concentration sensor 1c according to this variation differs from functional water concentration sensor 1 illustrated in FIG. 1 in that phosphor 20c is provided instead of phosphor 20, and exit window 42c is provided instead of exit window 42 in container 40.

Phosphor 20c is provided at exit window 42c of container 40. For example, exit window 42c is made of phosphor-containing glass containing phosphor 20c. Phosphor particles are dispersively contained in exit window 42c.

As described above, in functional water concentration sensor 1c according to this variation, phosphor 20c and exit window 42c are integrated, with it being possible to shorten the distance between container 40 and light-receiving element 30. Functional water concentration sensor 1c can thus be reduced in size. In addition, stray light of fluorescence 21 exiting from exit window 42c can be reduced to enhance detection accuracy.

[Variation 4]

Figure 12:
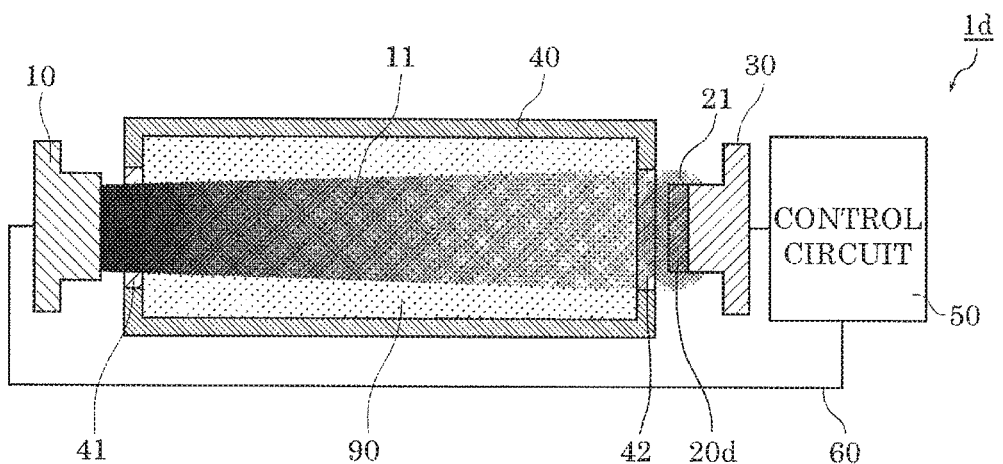
FIG. 12 is a schematic diagram illustrating the structure and operation of a functional water concentration sensor according to Variation 4 of Embodiment 1 of the present invention.

FIG. 12 is a schematic diagram illustrating the structure and operation of functional water concentration sensor 1d according to Variation 4 of this embodiment.

Functional water concentration sensor 1d according to this variation differs from functional water concentration sensor 1 illustrated in FIG. 1 in that phosphor 20d is provided instead of phosphor 20.

Phosphor 20d is provided on the surface of light-receiving element 30. In detail, phosphor 20d is contained in a resin material applied to the surface of light-receiving element 30. The resin material is, for example, a material having light-transmitting property such as silicone resin.

As described above, in functional water concentration sensor 1d according to this variation, phosphor 20d is provided on the surface of light-receiving element 30, so that the amount of fluorescence 21 received from phosphor 20d can be increased. Stray light of fluorescence 21 exiting from exit window 42c can thus be reduced to enhance detection accuracy. Moreover, the distance between container 40 and light-receiving element 30 can be shortened to reduce functional water concentration sensor 1d in size.

Embodiment 2

Figure 13:
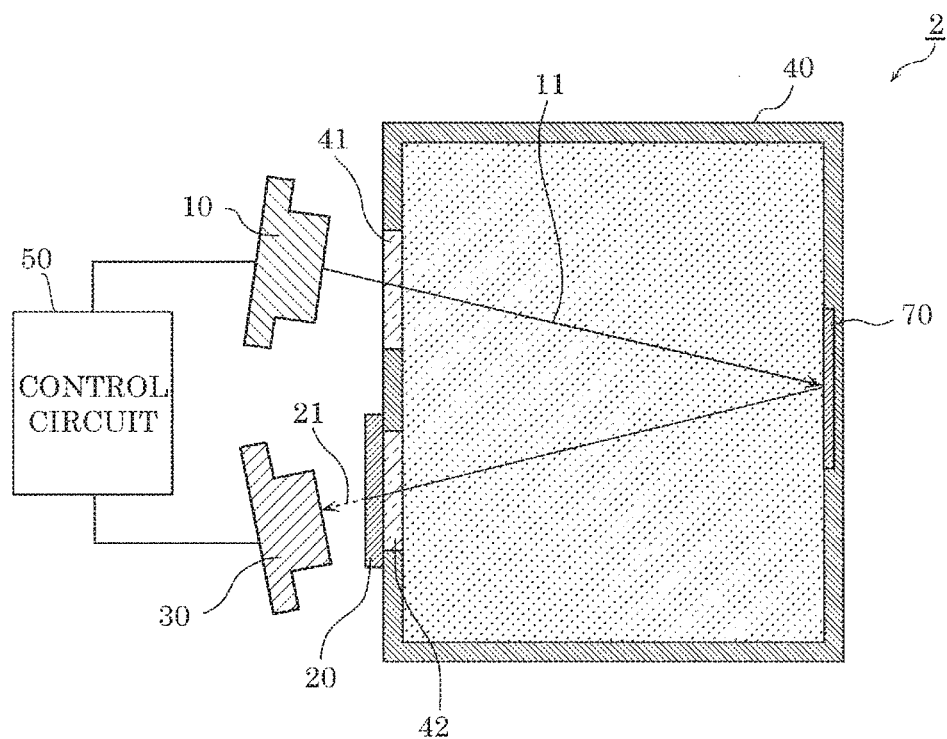
FIG. 13 is a schematic diagram illustrating the structure and operation of a functional water concentration sensor according to Embodiment 2 of the present invention.

The following describes a functional water concentration sensor according to Embodiment 2, with reference to FIG. 13. The differences from foregoing Embodiment 1 are mainly described below, while omitting or abridging the description of the same parts as in Embodiment 1.

FIG. 13 is a schematic diagram illustrating the structure and operation of functional water concentration sensor 2 according to this embodiment. As illustrated in FIG. 13, functional water concentration sensor 2 differs from functional water concentration sensor 1 according to Embodiment 1 in that reflector 70 is added.

[Reflector (First Reflector)]

Reflector 70 is an example of a first reflector that is located inside container 40 and reflects ultraviolet light 11. Reflector 70 specularly reflects ultraviolet light 11. In detail, reflector 70 reflects ultraviolet light 11 emitted from light source 10 and passed through entrance window 41, toward phosphor 20. Reflected ultraviolet light 11 passes through exit window 42 and enters phosphor 20, thus exciting phosphor 20. Excited phosphor 20 emits fluorescence 21 which enters light-receiving element 30. With the provision of reflector 70, the optical path length of ultraviolet light 11 is about twice the width of container 40 as illustrated in FIG. 13.

Reflector 70 is an inner surface of container 40. In detail, reflector 70 is formed by mirror-like treating the inner surface of container 40. For example, in the case where container 40 is made of a metal material, its inner surface is mirror-like treated by polishing, to form reflector 70. In the case where container 40 is made of a resin material, a metal evaporated film or the like is formed on its inner surface, to form reflector 70.

Reflector 70 may be an object other than container 40. In detail, reflector 70 may be a reflector plate placed at a predetermined position of container 40. Reflector 70 may be, for example, a glass plate or resin plate whose surface is mirror-like treated. Reflector 70 is fixed to the inner surface of container 40.

[Relationship Between Optical Path Length and Concentration]

Figure 14:
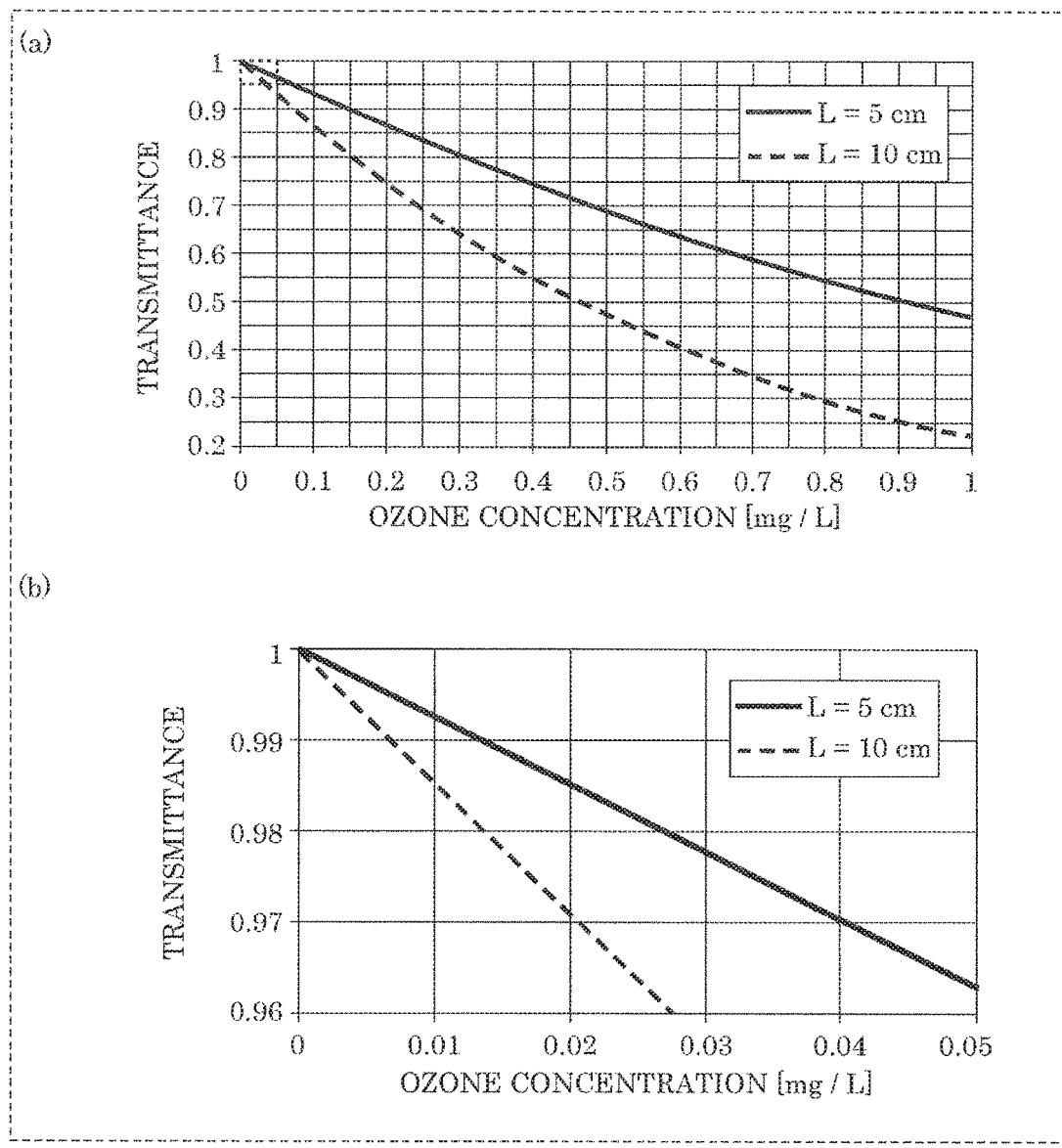
FIG. 14 is a diagram illustrating the transmittance of ultraviolet light with respect to the concentration of ozone water for each optical path length in the functional water concentration sensor according to Embodiment 2 of the present invention.

The following describes the result of measuring the relationship between the concentration and the transmittance for each optical path length in the case where functional water 90 is ozone water, with reference to FIG. 14. FIG. 14 is a diagram illustrating the transmittance of ultraviolet light 11 with respect to the concentration of ozone water for each optical path length in functional water concentration sensor 2 according to this embodiment.

In (a) and (b) in FIG. 14, the horizontal axis represents the concentration of ozone water (functional water 90), and the vertical axis represents the transmittance of ultraviolet light 11. (b) in FIG. 14 is an enlarged diagram of the range in which the ozone concentration is 0 mg/L to 0.05 mg/L and the transmittance is 0.96 to 1 (the dashed frame in (a) in FIG. 14).

As illustrated in FIG. 14, when the optical path length L is longer, the transmittance is lower. When the optical path length is longer, the time during which ultraviolet light 11 is transmitted is longer, and the time during which ultraviolet light 11 is in contact with functional water 90 is longer. This increases the amount of ultraviolet light 11 absorbed by functional water 90, and decreases the transmittance.

This tendency is seen even in the case where the concentration of ozone water is low. As illustrated in (b) in FIG. 14, the amount of change in transmittance is large even in the case where the concentration of ozone water is low. This facilitates the detection of a change in transmittance. Since the detection resolution increases, the concentration of ozone water can be accurately measured based on the transmittance.

[Advantageous Effects, Etc.]

As described above, functional water concentration sensor 2 according to this embodiment further includes reflector 70 that is located inside container 40 and reflects ultraviolet light 11.

Reflector 70 located inside container 40 reflects ultraviolet light 11 inside container 40, thus increasing the optical path length of ultraviolet light 11. Even in the case where the concentration of functional water 90 is low and the absorbance is low, a lot of ultraviolet light 11 is absorbed by increasing the optical path length of ultraviolet light 11. As a result, a change in intensity of ultraviolet light 11 can be detected by light-receiving element 30. In other words, the measurement range of the concentration of functional water 90 can be widened. The measurable concentration range can thus be widened without increasing the size of functional water concentration sensor 2.

For example, reflector 70 is an inner surface of container 40.

Since the inner surface of container 40 is used as reflector 70, another member is unnecessary, and therefore the cost can be reduced. Moreover, the space in container 40 can be used more effectively than in the case where a reflector plate or the like is provided as another member. For example, a longer optical path length is attained.

Functional water concentration sensor 2 according to this embodiment may not include phosphor 20. In detail, light-receiving element 30 may be a photodiode having sensitivity in the ultraviolet region, and directly detect ultraviolet light 11 transmitted through functional water 90. Even in such a case, according to this embodiment, the measurable concentration range can be widened or measurement accuracy can be enhanced without an increase in size. Functional water concentration sensor 2 can thus be reduced in size and increased in accuracy and sensitivity.

The following describes variations of functional water concentration sensor 2 according to this embodiment, with reference to drawings. In each variation, the description of the same parts as those of functional water concentration sensor 2 according to this embodiment is omitted or abridged.

[Variation 1]

Figure 15:
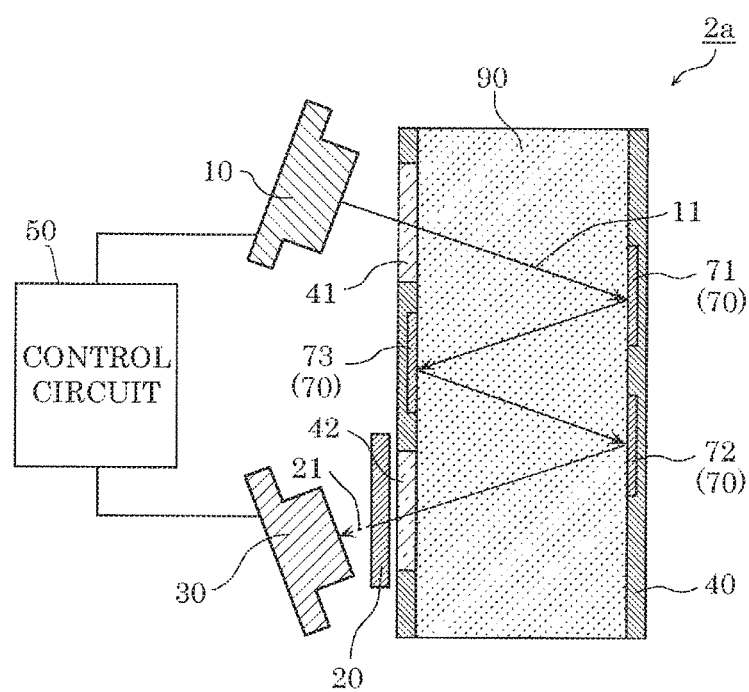
FIG. 15 is a schematic diagram illustrating the structure and operation of a functional water concentration sensor according to Variation 1 of Embodiment 2 of the present invention.

FIG. 15 is a schematic diagram illustrating the structure and operation of functional water concentration sensor 2a according to Variation 1 of this embodiment.

Functional water concentration sensor 2a according to this variation differs from functional water concentration sensor 2 illustrated in FIG. 13 in that a plurality of reflectors 70 are provided. The plurality of reflectors 70 are arranged to cause multiple reflection of ultraviolet light 11.

FIG. 15 illustrates an example where functional water 90 flows inside container 40, i.e. container 40 is a part of piping forming the flow path of functional water 90. The shape of container 40, i.e. the shape of the piping, is, for example, a circular cylinder or a rectangular cylinder, although not limited to such. For example, functional water 90 flows in the vertical direction of the paper in FIG. 15. The same applies to Variations 2 to 5 below.

In this variation, functional water concentration sensor 2a includes three reflectors 71 to 73 as the plurality of reflectors 70. The function, material, etc. of each of reflectors 71 to 73 are the same as those of reflector 70 in FIG. 13. Reflectors 71 and 72 are provided at the opposite inner surface of container 40 to light source 10 and light-receiving element 30. Reflector 73 is provided at the inner surface of container 40 on the same side as light source 10 and light-receiving element 30.

As illustrated in FIG. 15, reflector 71 reflects ultraviolet light 11 emitted from light source 10 and passed through entrance window 41, toward reflector 73. Reflector 73 reflects ultraviolet light 11 reflected by reflector 71, toward reflector 72. Reflector 72 reflects ultraviolet light 11 reflected by reflector 73, toward phosphor 20. Ultraviolet light 11 reflected by reflector 72 passes through exit window 42 and enters phosphor 20, thus exciting phosphor 20.

As described above, functional water concentration sensor 2a according to this variation includes a plurality of first reflectors 70, and the plurality of reflectors 70 are arranged to cause multiple reflection of ultraviolet light 11.

Since three reflectors 71 to 73 multiple-reflect ultraviolet light 11, the optical path length of ultraviolet light 11 traveling inside container 40 can be made longer. A longer optical path length allows a lower concentration of functional water 90 to be measured. Functional water concentration sensor 2a can thus be increased in sensitivity.

In this variation, the whole inner surface of container 40 may be mirror-like treated.

[Variation 2]

Figure 16:
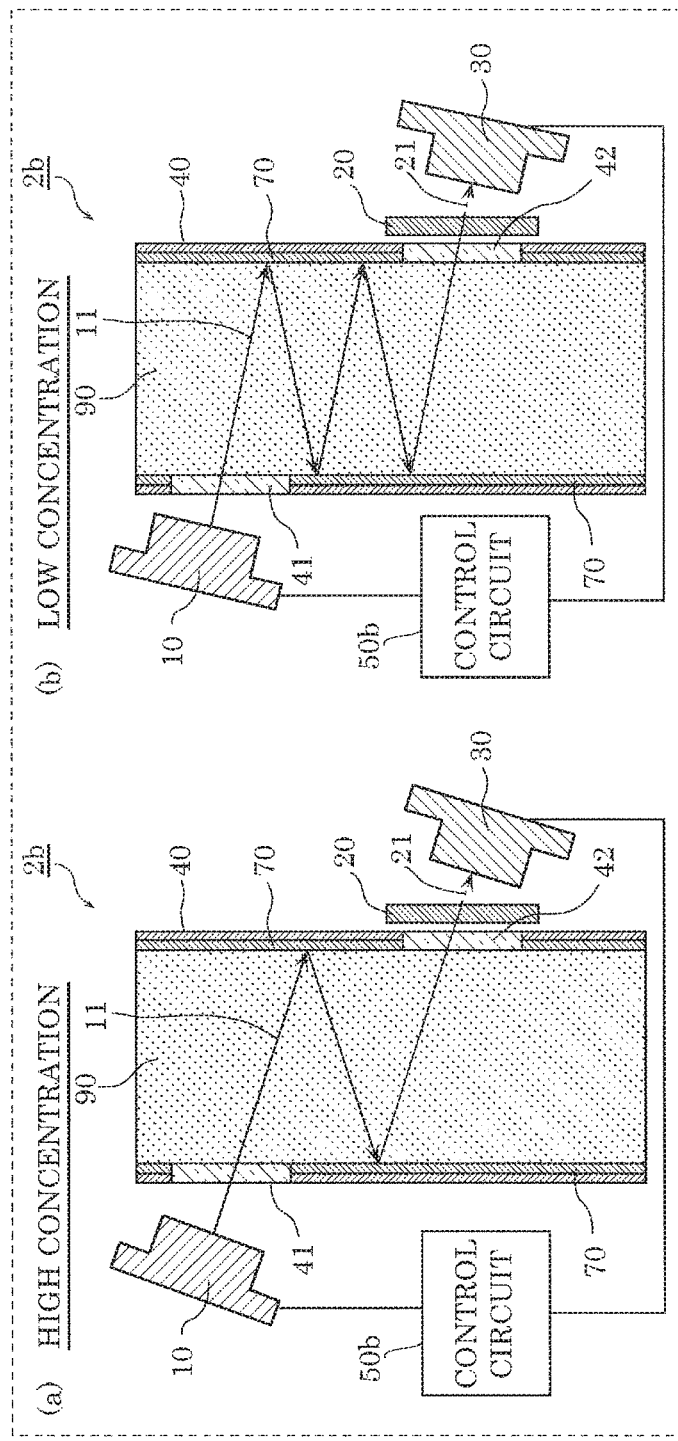
FIG. 16 is a schematic diagram illustrating the structure and operation of a functional water concentration sensor according to Variation 2 of Embodiment 2 of the present invention.

FIG. 16 is a schematic diagram illustrating the structure and operation of functional water concentration sensor 2b according to Variation 2 of this embodiment. In functional water concentration sensor 2b according to this variation, the position or orientation of light source 10 and light-receiving element 30 is variable depending on the concentration of functional water 90. In FIG. 16, (a) illustrates the case where the concentration of functional water 90 is high, and (b) illustrates the case where the concentration of functional water 90 is low.

Functional water concentration sensor 2b according to this variation differs from functional water concentration sensor 2 illustrated in FIG. 13 in that control circuit 50b is provided instead of control circuit 50. Moreover, reflector 70 is provided at the whole inner surface of container 40. Reflector 70 may be provided not at the whole inner surface of container 40, as long as it is located in the range irradiated with ultraviolet light 11.

Control circuit 50b changes the position or orientation of at least one of light source 10 and light-receiving element 30 depending on the concentration of functional water 90, in addition to the functions of control circuit 50. The at least one of light source 10 and light-receiving element 30 is provided with, for example, a mobile mechanism (not illustrated) such as an actuator. Control circuit 50b changes the position or orientation of the at least one of light source 10 and light-receiving element 30 via the actuator. In this way, control circuit 50b changes the optical path length from light source 10 to light-receiving element 30. The optical path length corresponds to the length of transmission of ultraviolet light 11 through functional water 90, i.e. the distance from the entrance of ultraviolet light 11 into functional water 90 via entrance window 41 to the entrance of ultraviolet light 11 into exit window 42.

In detail, in the case where the concentration of functional water 90 is high, control circuit 50b changes the position or orientation of light source 10 or light-receiving element 30 so as to shorten the optical path length, as illustrated in (a) in FIG. 16. In this variation, control circuit 50b changes the orientation of light source 10 so as to reduce the number of times ultraviolet light 11 is reflected in container 40. In detail, control circuit 50b changes the orientation of light source 10 so that the incidence angle of ultraviolet light 11 emitted from light source 10 with respect to entrance window 41 is larger, i.e. ultraviolet light 11 enters entrance window 41 more obliquely.

Here, control circuit 50b changes the orientation of light-receiving element 30 depending on the direction of ultraviolet light 11 exiting from exit window 42. In detail, control circuit 50b changes the orientation of light-receiving element 30 so that ultraviolet light 11 is incident on the light-receiving surface perpendicularly. In this embodiment, phosphor 20 is provided, and light-receiving element 30 receives not ultraviolet light 11 but fluorescence 21. Since phosphor 20 emits fluorescence 21 omnidirectionally, control circuit 50b does not need to change the orientation of light-receiving element 30.

In the case where the concentration of functional water 90 is low, control circuit 50b changes the position or orientation of light source 10 or light-receiving element 30 so as to increase the optical path length, as illustrated in (b) in FIG. 16. In this variation, control circuit 50b changes the orientation of light source 10 so as to increase the number of times ultraviolet light 11 is reflected in container 40. In detail, control circuit 50b changes the orientation of light source 10 so that the incidence angle of ultraviolet light 11 emitted from light source 10 with respect to entrance window 41 is smaller, i.e. ultraviolet light 11 enters entrance window 41 at an angle closer to the right angle (perpendicular). Here, control circuit 50b may change the orientation of light-receiving element 30. In this variation, however, fluorescence 21 is detected as mentioned above, and so control circuit 50b does not need to change the orientation of light-receiving element 30.

Based on a predicted value (e.g. previous measurement) of the concentration of functional water 90, control circuit 50b changes the position or orientation of light source 10 or light-receiving element 30 so that the optical path length from light source 10 to light-receiving element 30 is an optical path length that enables optimal measurement of concentration around the predicted value.

For example, in the case where the concentration of functional water 90 is excessively high, ultraviolet light 11 is mostly absorbed. As a result, light-receiving element 30 can hardly receive fluorescence 21. In the case where light-receiving element 30 can hardly receive fluorescence 21, the optical path length is shortened to reduce the absorption of ultraviolet light 11 by functional water 90. This allows light-receiving element 30 to receive fluorescence 21. A higher concentration of functional water 90 can thus be measured.

In the case where the concentration of functional water 90 is excessively low, on the other hand, ultraviolet light 11 is mostly not absorbed. As a result, the amount of fluorescence 21 detected by light-receiving element 30 can be approximately the same as in the case where there is no functional water 90, or can exceed the detection range of light-receiving element 30 and become saturated. In such a case, the optical path length is increased to facilitate the absorption of ultraviolet light 11 by functional water 90. This allows light-receiving element 30 to receive an appropriate amount of fluorescence 21. A lower concentration of functional water 90 can thus be measured.

As described above, functional water concentration sensor 2b according to this variation further includes control circuit 50b that changes an optical path length from light source 10 to light-receiving element 30, by changing a position or an orientation of at least one of light source 10 and light-receiving element 30 depending on a concentration of functional water 90.

This improves the measurement accuracy of the concentration of functional water 90, and widens the measurement range.

[Variation 3]

Figure 17:
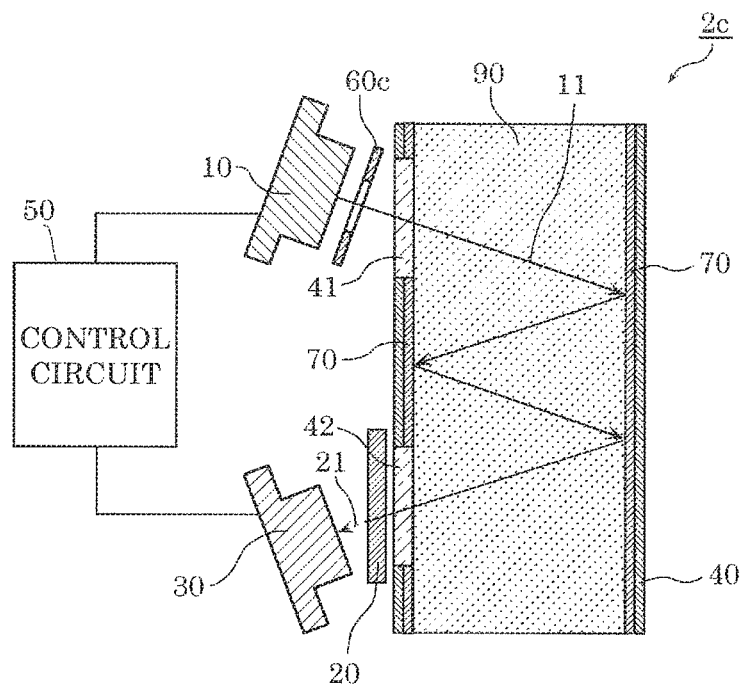
FIG. 17 is a schematic diagram illustrating the structure and operation of a functional water concentration sensor according to Variation 3 of Embodiment 2 of the present invention.

FIG. 17 is a schematic diagram illustrating the structure and operation of functional water concentration sensor 2c according to Variation 3 of this embodiment.

Functional water concentration sensor 2c according to this variation differs from functional water concentration sensor 2 illustrated in FIG. 13 in that slit portion 60c is added.

Slit portion 60c is located between light source 10 and entrance window 41, and limits the application range of ultraviolet light 11. In this variation, slit portion 60c is an example of a collimator portion that converts ultraviolet light 11 into parallel light. In detail, ultraviolet light 11 emitted from light source 10 is converted into parallel light as a result of passing through an opening of slit portion 60c. Slit portion 60c is, for example, a plate having an opening (slit).

Slit portion 60c is made of a material that blocks (reflects or absorbs) ultraviolet light 11. For example, slit portion 60c is made of the same material as the body of container 40.

As described above, in functional water concentration sensor 2c according to this variation, slit portion 60c converts ultraviolet light 11 into parallel light. This suppresses the attenuation of ultraviolet light 11, and enhances the use efficiency of ultraviolet light 11. Consequently, the measurable concentration range can be widened, or concentration measurement accuracy can be enhanced. In this variation, the collimator mechanism can be achieved by a simple structure such as a plate having an opening. Functional water concentration sensor 2c can thus be reduced in size and cost.

[Variation 4]

Figure 18:
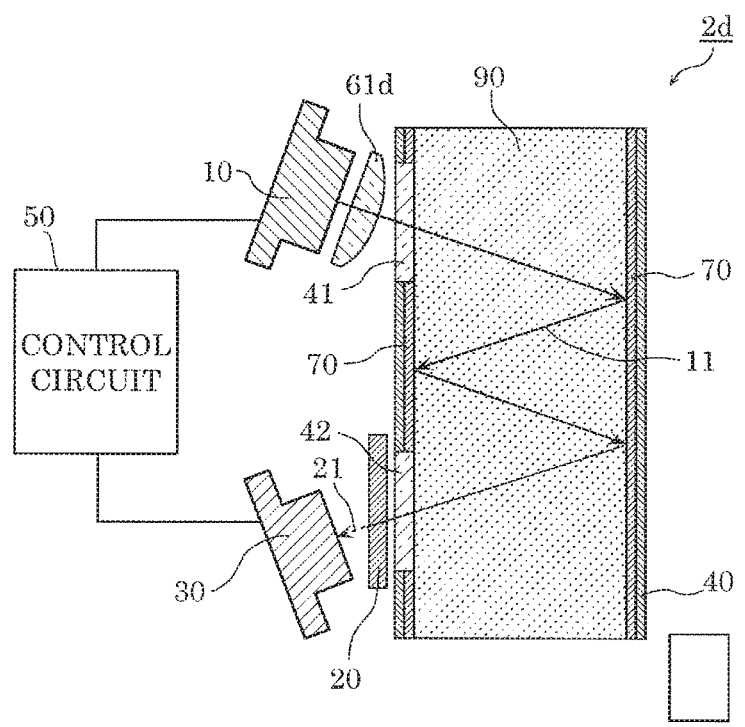
FIG. 18 is a schematic diagram illustrating the structure and operation of a functional water concentration sensor according to Variation 4 of Embodiment 2 of the present invention.

FIG. 18 is a schematic diagram illustrating the structure and operation of functional water concentration sensor 2d according to Variation 4 of this embodiment.

Functional water concentration sensor 2d according to this variation differs from functional water concentration sensor 2 illustrated in FIG. 13 in that lens portion 61d is added.

Lens portion 61d is located between light source 10 and entrance window 41, and limits the application range of ultraviolet light 11. In this variation, lens portion 61d is an example of a collimator portion that converts ultraviolet light 11 into parallel light. In detail, ultraviolet light 11 emitted from light source 10 is converted into parallel light as a result of passing through lens portion 61d. Lens portion 61d is a collimator lens, and is made of silica glass having light-transmitting property as an example.

As described above, in functional water concentration sensor 2d according to this variation, lens portion 61d converts ultraviolet light 11 into parallel light. This suppresses the attenuation of ultraviolet light 11, and enhances the use efficiency of ultraviolet light 11. Consequently, the measurable concentration range can be widened, or concentration measurement accuracy can be enhanced. In this variation, the collimator mechanism can be achieved by a simple structure. Functional water concentration sensor 2d can thus be reduced in size and cost.

[Variation 5]

Figure 19:
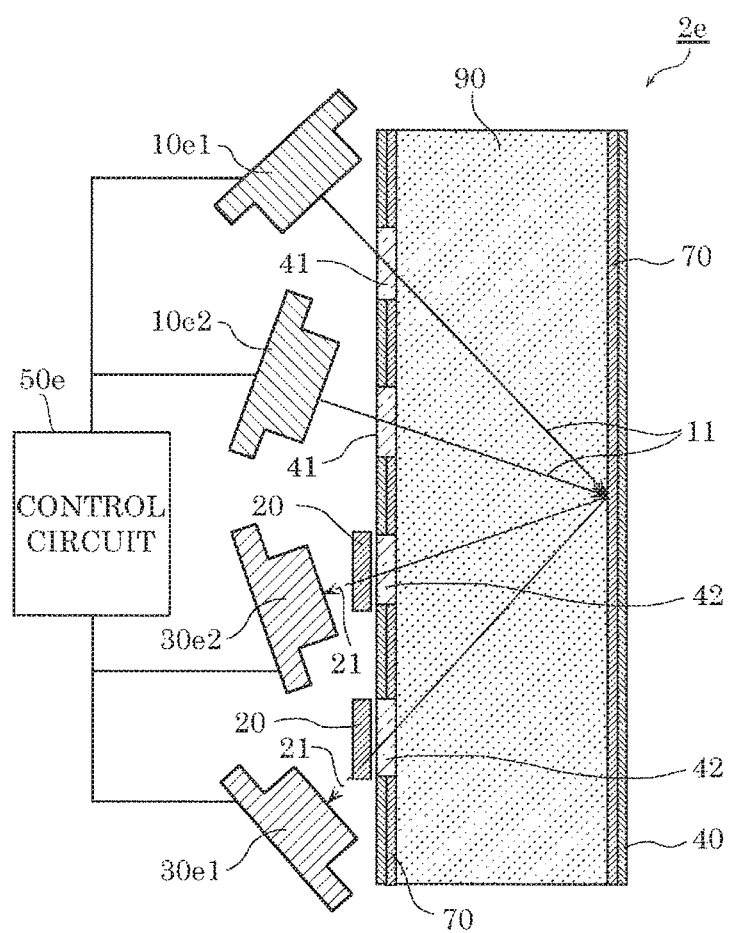
FIG. 19 is a schematic diagram illustrating the structure and operation of a functional water concentration sensor according to Variation 5 of Embodiment 2 of the present invention.

FIG. 19 is a schematic diagram illustrating the structure and operation of functional water concentration sensor 2e according to Variation 5 of this embodiment.

Functional water concentration sensor 2e according to this variation differs from functional water concentration sensor 2 illustrated in FIG. 13 in that a plurality of pairs of light sources 10 and light-receiving elements 30 are provided and control circuit 50e is provided instead of control circuit 50.

In this variation, a plurality of light sources 10 and a plurality of light-receiving elements 30 are arrayed. For example, the plurality of light sources 10 are one-dimensionally arrayed along the direction in which functional water 90 flows. The plurality of light sources 10 may be two-dimensionally or three-dimensionally arrayed. The same applies to the plurality of light-receiving elements 30.

As illustrated in FIG. 19, functional water concentration sensor 2e includes light sources 10e1 and 10e2 as the plurality of light sources 10. Functional water concentration sensor 2e also includes light-receiving elements 30e1 and 30e2 as the plurality of light-receiving elements 30. Light sources 10e1 and 10e2 and light-receiving elements 30e1 and 30e2 have the same functions as light source 10 and light-receiving element 30.

In this variation, light source 10e1 and light-receiving element 30e1 are associated with each other, and light source 10e2 and light-receiving element 30e2 are associated with each other. In other words, light source 10e1 and light-receiving element 30e1 form a pair (e.g. a first pair), and light source 10e2 and light-receiving element 30e2 form another pair (e.g. a second pair). In detail, ultraviolet light 11 emitted from light source 10e1 enters light-receiving element 30e1, and ultraviolet light 11 emitted from light source 10e2 enters light-receiving element 30e2.

The plurality of pairs of light sources 10 and light-receiving elements 30 are arranged each to have a different optical path length from light source 10 to light-receiving element 30. As illustrated in FIG. 19, the optical path length of the pair (first pair) of light source 10e1 and light-receiving element 30e1 is longer than the optical path length of the pair (second pair) of light source 10e2 and light-receiving element 30e2.

Control circuit 50e selects a pair from the plurality of pairs of light sources 10 and light-receiving elements 30 depending on the concentration of functional water 90, in addition to the functions of control circuit 50. In this way, control circuit 50e changes the optical path length depending on the concentration of functional water 90.

For example, in the case where the concentration of functional water 90 is high, control circuit 50e selects the pair (first pair) of light source 10e1 and light-receiving element 30e1 longer in optical path length. In the case where the concentration of functional water 90 is low, control circuit 50e selects the pair (second pair) of light source 10e2 and light-receiving element 30e2 shorter in optical path length.

As described above, functional water concentration sensor 2e according to this variation includes a plurality of pairs of light sources 10 and light-receiving elements 30. The plurality of pairs of light sources 10 and light-receiving elements 30 are arranged each to have a different optical path length from light source 10 to light-receiving element 30. Functional water concentration sensor 2e further includes control circuit 50e that selects a pair from the plurality of pairs depending on a concentration of functional water 90.

By selecting an appropriate pair depending on the concentration as in the case of changing the position or orientation of light source 10 or light-receiving element 30 (Variation 2 of this embodiment), an appropriate optical path length can be selected. This improves the measurement accuracy of the concentration of functional water 90, and widens the measurement range.

Embodiment 3

Figure 20:
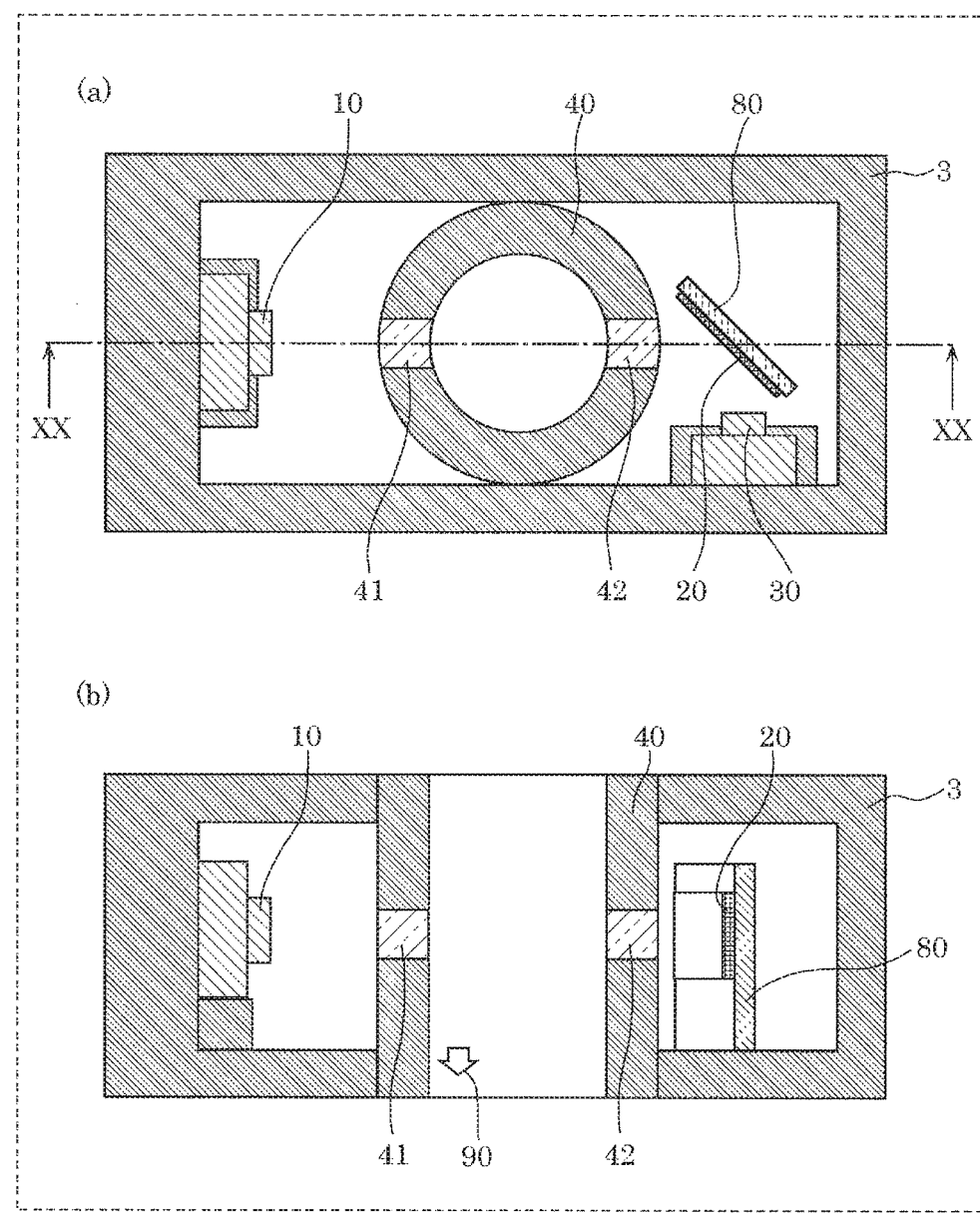
FIG. 20 is a schematic diagram illustrating the structure of a functional water concentration sensor according to Embodiment 3 of the present invention.

The following describes a functional water concentration sensor according to Embodiment 3, with reference to FIG. 20. The differences from foregoing Embodiment 1 are mainly described below, while omitting or abridging the description of the same parts as in Embodiment 1.

FIG. 20 is a schematic diagram illustrating the structure of functional water concentration sensor 3 according to this embodiment. In detail, (a) in FIG. 20 is a sectional view of functional water concentration sensor 3, and illustrates a section orthogonal to the direction in which functional water 90 flows inside container 40 constituting a part of piping. (b) in FIG. 20 illustrates a section along line XX-XX in (a). Functional water 90 flows in the thickness direction of the paper in (a), and flows in the vertical direction of the paper in (b) (see the hollow arrow).

As illustrated in FIG. 20, functional water concentration sensor 3 differs from functional water concentration sensor 1 according to Embodiment 1 in that reflector 80 is added.

[Reflector (Second Reflector)]

Reflector 80 is an example of a second reflector that has a reflection surface provided with phosphor 20, and reflects fluorescence 21 by the reflection surface toward light-receiving element 30. Reflector 80 is located outside container 40.

In detail, reflector 80 is a reflector plate located outside container 40. Reflector 80 is, for example, a glass plate or resin plate at least one main surface (reflection surface) of which is mirror-like treated. The reflection surface of reflector 80 is coated with a resin material containing phosphor 20.

Although this embodiment describes an example where the reflection surface is coated with a resin material containing phosphor 20, this is not a limitation. For example, a glass plate containing phosphor 20 may be attached to the reflection surface.

[Advantageous Effects, Etc.]

As described above, functional water concentration sensor 3 according to this embodiment further includes reflector 80 that has a reflection surface provided with phosphor 20, is located outside container 40, and reflects fluorescence 21 by the reflection surface toward light-receiving element 30.

For example, with the structure in Embodiment 1 or the like, about half of fluorescence 21 emitted from phosphor 20 is directed toward exit window 42 and does not enter light-receiving element 30. In this embodiment, on the other hand, reflector 80 reflects fluorescence 21 toward light-receiving element 30, so that more fluorescence 21 can enter light-receiving element 30. Fluorescence 21 emitted from phosphor 20 can be used effectively in this way. Even in the case where the intensity of ultraviolet light 11 is weak and the intensity of fluorescence 21 is weak, light-receiving element 30 can receive a lot of light, enabling the measurement of the concentration of functional water 90. The measurable range of the concentration of functional water 90 can thus be widened.

The following describes variations of functional water concentration sensor 3 according to this embodiment, with reference to drawings. In each variation, the description of the same parts as those of functional water concentration sensor 3 according to this embodiment is omitted or abridged.

[Variation 1]

Figure 21:
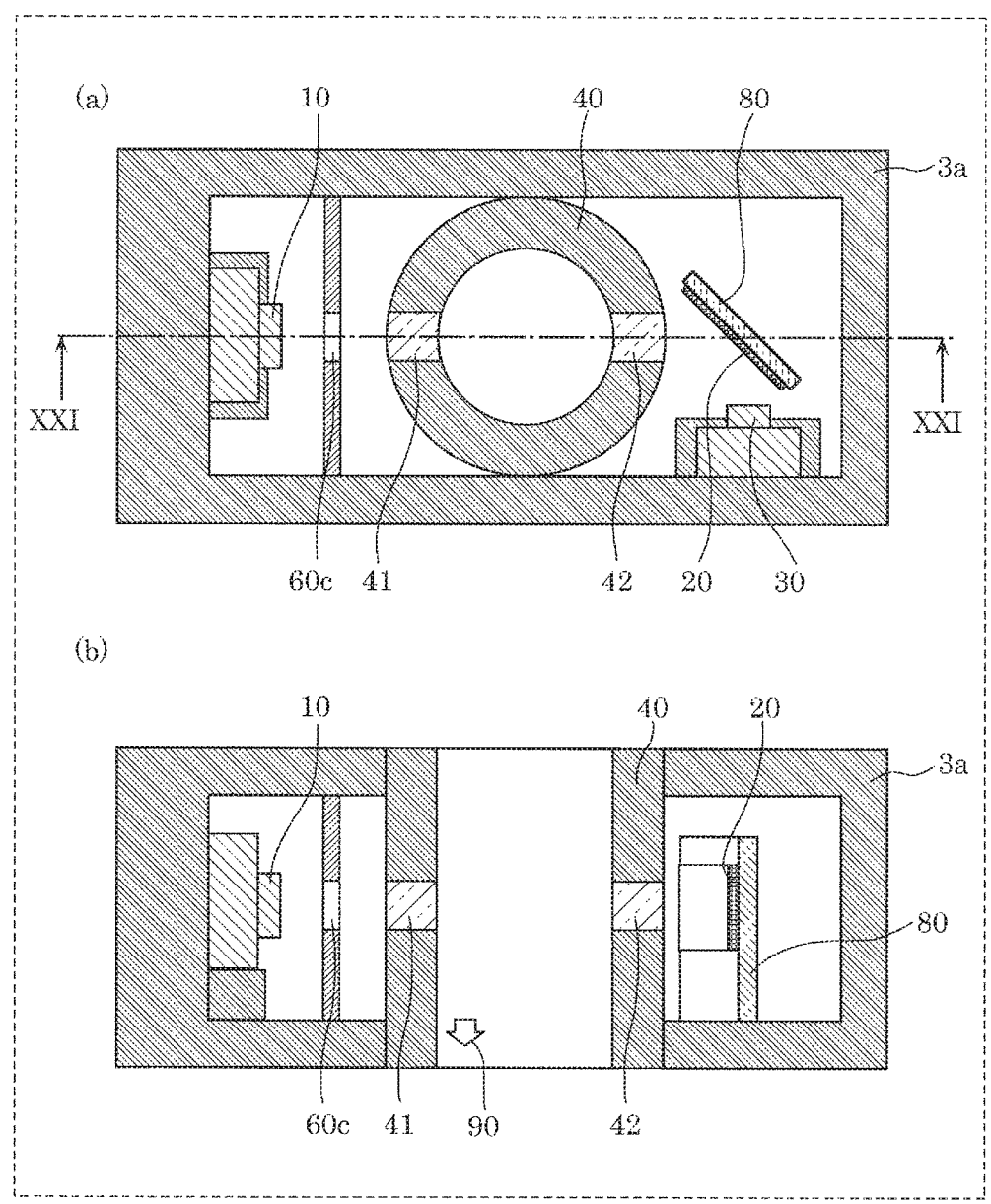
FIG. 21 is a schematic diagram illustrating the structure of a functional water concentration sensor according to Variation 1 of Embodiment 3 of the present invention.

FIG. 21 is a schematic diagram illustrating the structure of functional water concentration sensor 3a according to Variation 1 of this embodiment. In detail, (a) in FIG. 21 is a sectional view of functional water concentration sensor 3a, and illustrates a section orthogonal to the direction in which functional water 90 flows inside container 40 constituting a part of piping. (b) in FIG. 21 illustrates a section along line XXI-XXI in (a).

Functional water concentration sensor 3a according to this variation differs from functional water concentration sensor 3 illustrated in FIG. 20 in that slit portion 60c is added. Slit portion 60c is the same as that in Variation 3 in Embodiment 2.

As described above, in functional water concentration sensor 3a according to this variation, slit portion 60c converts ultraviolet light 11 into parallel light. This suppresses the attenuation of ultraviolet light 11, and enhances the use efficiency of ultraviolet light 11. Consequently, the measurable concentration range can be widened, or concentration measurement accuracy can be enhanced. In this variation, the collimator mechanism can be achieved by a simple structure such as a plate having an opening. Functional water concentration sensor 3a can thus be reduced in size and cost.

[Variation 2]

Figure 22:
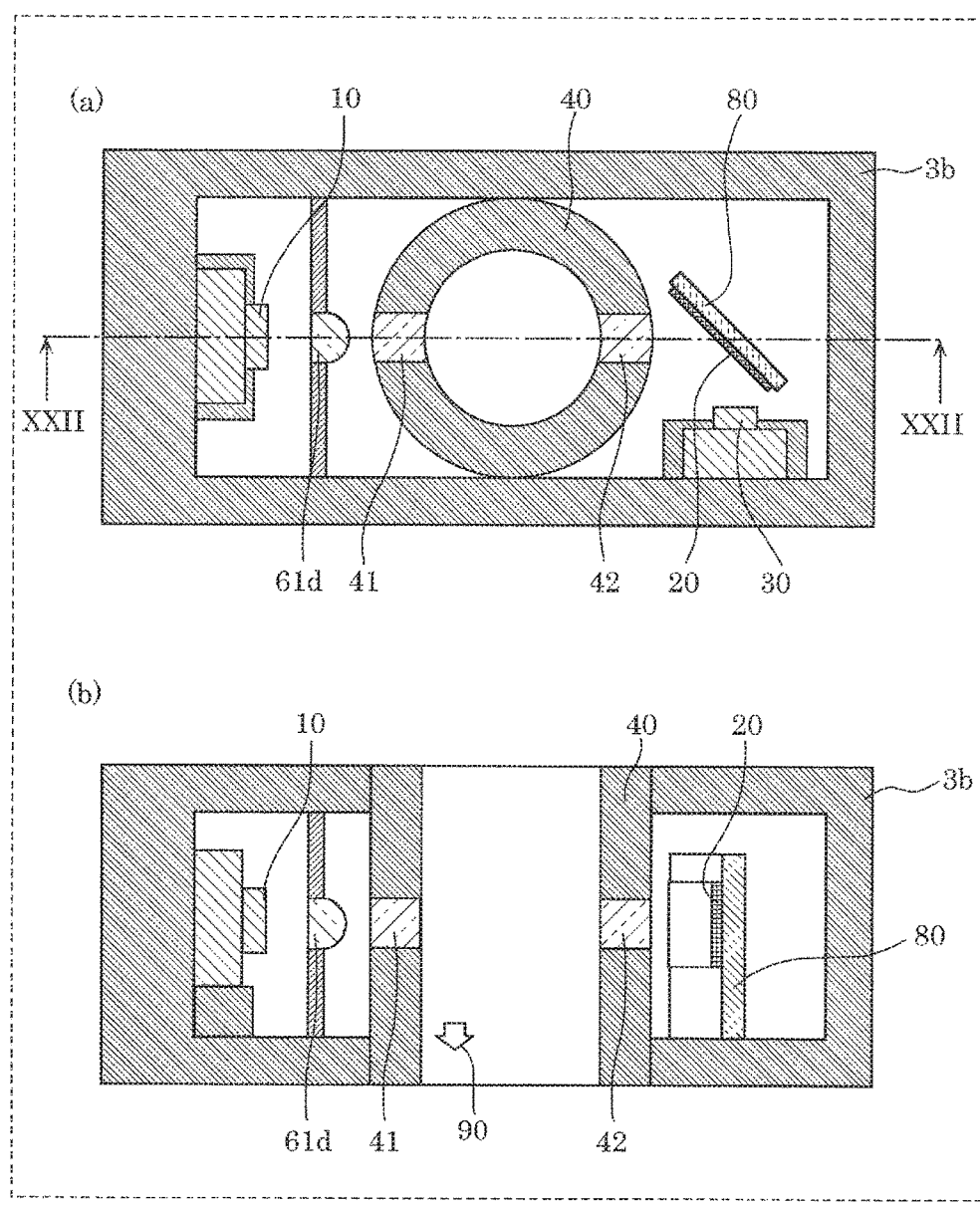
FIG. 22 is a schematic diagram illustrating the structure of a functional water concentration sensor according to Variation 2 of Embodiment 3 of the present invention.

FIG. 22 is a schematic diagram illustrating the structure of functional water concentration sensor 3b according to Variation 2 of this embodiment. In detail, (a) in FIG. 22 is a sectional view of functional water concentration sensor 3b, and illustrates a section orthogonal to the direction in which functional water 90 flows inside container 40 constituting a part of piping. (b) in FIG. 22 illustrates a section along line XXII-XXII in (a).

Functional water concentration sensor 3b according to this variation differs from functional water concentration sensor 3 illustrated in FIG. 20 in that lens portion 61d is added. Lens portion 61d is the same as that in Variation 4 in Embodiment 2.

As described above, in functional water concentration sensor 3b according to this variation, lens portion 61d converts ultraviolet light 11 into parallel light. This suppresses the attenuation of ultraviolet light 11, and enhances the use efficiency of ultraviolet light 11. Consequently, the measurable concentration range can be widened, or concentration measurement accuracy can be enhanced. In this variation, the collimator mechanism can be achieved by a simple structure. Functional water concentration sensor 3b can thus be reduced in size and cost.

[Variation 3]

Figure 23:
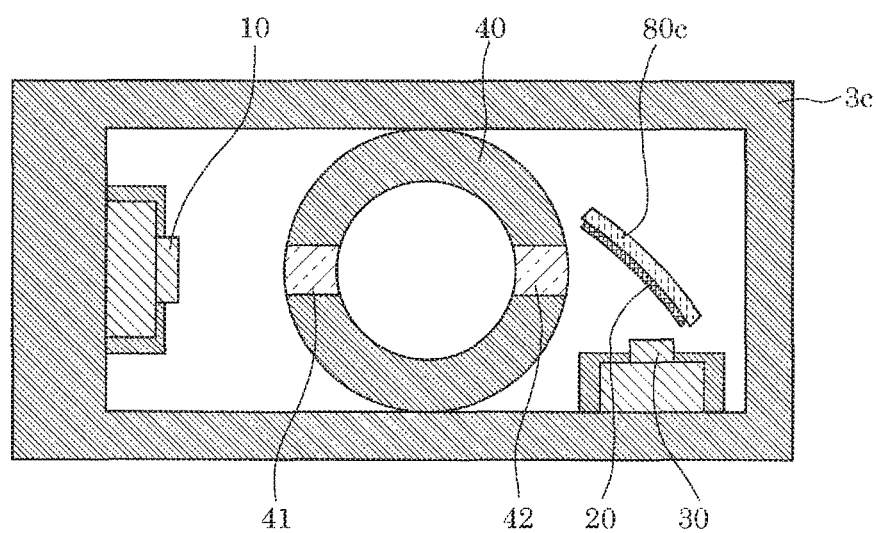
FIG. 23 is a schematic diagram illustrating the structure of a functional water concentration sensor according to Variation 3 of Embodiment 3 of the present invention.

FIG. 23 is a schematic diagram illustrating the structure of functional water concentration sensor 3c according to Variation 3 of this embodiment. In detail, FIG. 23 is a sectional view of functional water concentration sensor 3c, and illustrates a section orthogonal to the direction in which functional water 90 flows inside container 40 constituting a part of piping.

Functional water concentration sensor 3c according to this variation differs from functional water concentration sensor 3 illustrated in FIG. 20 in that reflector 80c is provided instead of reflector 80.

Reflector 80c is a concave mirror. In detail, reflector 80c is an elliptic mirror having a focal point at light-receiving element 30. In other words, the reflection surface of reflector 80c is a part of an ellipsoid. Reflector 80c may be, for example, a parabolic mirror whose reflection surface is a paraboloid.

This allows more fluorescence 21 to enter light-receiving element 30, so that the measurable range of the concentration of functional water 90 can be widened.

(Other Modifications)

While the functional water concentration sensor according to the present invention has been described above by way of embodiments and variations, the present invention is not limited to the foregoing embodiments.

For example, although the foregoing embodiments describe the case where light source 10 and light-receiving element 30 are located outside container 40, this is not a limitation. For example, light source 10 may be attached to entrance window 41. In other words, the light-emitting surface of light source 10 may be exposed to the inside of container 40. Likewise, light-receiving element 30 may be attached to exit window 42. In other words, the light-receiving surface of light-receiving element 30 may be exposed to the inside of container 40. In such a case, phosphor 20 is also located inside container 40. Alternatively, light source 10 and light-receiving element 30 may be located inside container 40. In such a case, entrance window 41 and exit window 42 of container 40 may be omitted.

Other modifications obtained by applying various changes conceivable by a person skilled in the art to the foregoing embodiments and any combinations of the structural elements and functions in the foregoing embodiments without departing from the scope of the present invention are also included in the present invention.

The invention claimed is:

1. A functional water concentration sensor comprising:
   a container used to contain functional water;
   a light source that emits ultraviolet light;
   a phosphor that emits fluorescence when excited by ultraviolet light emitted from the light source and transmitted through the container; and
   a light-receiving element that receives the fluorescence,
   wherein a peak wavelength of the ultraviolet light emitted from the light source is in a predetermined range that includes an absorption peak specific to the functional water.

2. The functional water concentration sensor according to claim 1,
   wherein the phosphor emits light having a peak wavelength corresponding to sensitivity of the light-receiving element, as the fluorescence.

3. The functional water concentration sensor according to claim 1,
   wherein the light-receiving element is located in proximity to the phosphor.

4. The functional water concentration sensor according to claim 1,
   wherein the light source, the container, the phosphor, and the light-receiving element are arranged approximately in a same straight line in the stated order.

5. The functional water concentration sensor according to claim 1, further comprising
   a first reflector that is located inside the container and reflects the ultraviolet light.

6. The functional water concentration sensor according to claim 5, comprising
   a plurality of the first reflectors,
   wherein the plurality of the first reflectors are arranged to cause multiple reflection of the ultraviolet light.

7. The functional water concentration sensor according to claim 5, further comprising
a control circuit that changes an optical path length from the light source to the light-receiving element, by changing a position or an orientation of at least one of the light source and the light-receiving element depending on a concentration of the functional water.

8. The functional water concentration sensor according to claim 5,
wherein the first reflector is an inner surface of the container.

9. The functional water concentration sensor according to claim 5, comprising
a plurality of pairs of the light source and the light-receiving element,
wherein the plurality of pairs of the light source and the light-receiving element are arranged each to have a different optical path length from the light source to the light-receiving element, and
the functional water concentration sensor further comprises
a control circuit that selects a pair from the plurality of pairs depending on a concentration of the functional water.

10. The functional water concentration sensor according to claim 1, further comprising
a second reflector that has a reflection surface provided with the phosphor, is located outside the container, and reflects the fluorescence by the reflection surface toward the light-receiving element.

11. The functional water concentration sensor according to claim 10,
wherein the second reflector is a concave mirror.

12. The functional water concentration sensor according to claim 11,
wherein the second reflector is an elliptic mirror having a focal point at the light-receiving element.

13. The functional water concentration sensor according to claim 1,
wherein the container includes an entrance window which the ultraviolet light emitted from the light source enters, and
the functional water concentration sensor further comprises
a slit portion that is located between the light source and the entrance window, and limits an application range of the ultraviolet light.

14. The functional water concentration sensor according to claim 13,
wherein the slit portion has an opening having approximately a same shape as the entrance window.

15. The functional water concentration sensor according to claim 1,
wherein the container includes an entrance window which the ultraviolet light emitted from the light source enters, and
the functional water concentration sensor further comprises
a lens portion that is located between the light source and the entrance window, and suppresses divergence of the ultraviolet light.

16. The functional water concentration sensor according to claim 1,
wherein the container includes an entrance window which the ultraviolet light emitted from the light source enters, and
the functional water concentration sensor further comprises
a collimator portion that is located between the light source and the entrance window, and converts the ultraviolet light into parallel light.

17. The functional water concentration sensor according to claim 1,
wherein the container includes an entrance window which the ultraviolet light emitted from the light source enters, and
the ultraviolet light emitted from the light source enters the entrance window approximately perpendicularly.

* * * * *